US007105162B1

(12) United States Patent
Schmidt et al.

(10) Patent No.: US 7,105,162 B1
(45) Date of Patent: Sep. 12, 2006

(54) PHARMACEUTICAL COMPOSITION FOR IMMUNOMODULATION BASED ON PEPTIDES AND ADJUVANTS

(75) Inventors: Walter Schmidt, Vienna (AT); Max Birnstiel, Vienna (AT); Peter Steinlein, Vienna (AT); Michael Buschle, Brunn/Gebirge (AT); Tamàs Schweighoffer, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/125,672

(22) PCT Filed: Feb. 21, 1997

(86) PCT No.: PCT/EP97/00828

§ 371 (c)(1),
(2), (4) Date: Apr. 26, 1999

(87) PCT Pub. No.: WO97/30721

PCT Pub. Date: Aug. 28, 1997

(30) Foreign Application Priority Data

Feb. 24, 1996 (DE) ................................ 196 07 044
Sep. 19, 1996 (DE) ................................ 196 38 313
Nov. 25, 1996 (DE) ................................ 196 48 687

(51) Int. Cl.
*A61K 39/00* (2006.01)
(52) U.S. Cl. .................. 424/185.1; 424/85.1; 424/85.2; 424/186.1; 424/193.1; 424/195.1; 424/195.11; 424/196.11; 424/197.11; 424/277.1; 424/278.1; 424/280.1; 514/44
(58) Field of Classification Search ............. 424/185.1, 424/186.1, 85.1, 85.2, 278.1, 280.1, 193.1, 424/277.1; 530/328, 345, 351; 536/235; 514/2, 44
See application file for complete search history.

(56) References Cited

U.S. PATENT DOCUMENTS

| 4,728,639 | A | * | 3/1988 | Beachey ..................... 514/12 |
| 4,847,240 | A | * | 7/1989 | Ryser et al. |
| 4,956,273 | A | * | 9/1990 | Kennedy et al. ................ 435/5 |
| 5,409,703 | A | * | 4/1995 | McAnalley et al. |
| 5,571,711 | A | * | 11/1996 | Van Der Bruggen et al. |
| 5,650,152 | A | * | 7/1997 | Anderson et al. |
| 5,683,886 | A | * | 11/1997 | van der Bruggen et al. ............. 435/7.24 |
| 5,759,572 | A | * | 6/1998 | Sugimoto et al. |
| 6,001,809 | A | * | 12/1999 | Thorsett et al. |
| 6,022,544 | A | * | 2/2000 | Dintzis et al. ........... 424/193.1 |
| 6,660,276 | B1 | * | 12/2003 | Slingluff et al. ......... 424/277.1 |

FOREIGN PATENT DOCUMENTS

| EP | 0346 022 A1 | * | 12/1989 |
| GB | 1 290 141 | | 9/1972 |
| GB | 2 191 494 A | | 12/1987 |
| WO | WO 92/20356 | | 11/1992 |
| WO | WO 93/19768 | | 10/1993 |
| WO | WO 94/05304 | | 3/1994 |
| WO | WO 94/23031 | | 10/1994 |
| WO | WO 95/00159 | | 1/1995 |
| WO | WO 95/02398 | | 1/1995 |
| WO | WO 97/19169 | | 5/1997 |
| WO | WO 97/30721 | | 8/1997 |

OTHER PUBLICATIONS

Dorland's illustrated medical dictionary. 27th Edition, W. B. Saunders Co., Philadelphia, PA, p 823, 1988.*
Immunology An Illustrated Outline. Male. Gower Med. Publ. London, p. 73, 1986.*
Reddy et al. J. Immunol. Meth. vol. 141: 157-163, 1991.*
CAPLUS Abstract 125: 150981, 1996.*
Anderson et al. Nature. vol. 392, Suppl. 30: 25-30, 1998.*
Verma et al. Nature, vol. 389: 239-242, 1997.*
Mulligan et al. Science. vol. 260: 926-932, 1993.*
Bomford, R. et al., "Immunomodulation by Adjuvants," In: *Vaccines*, Gregoriadis, G. et al., eds., Plenum Press, New York, pp. 25-32 (1991).
Bronte, V. et al., "IL-2 Enhances the Function of Recombinant Poxvirus-Based Vaccines in the Treatment of Established Pulmonary Metastases," *J. Immunol.* 154:5282-5292 (1995).
Braciale, T.J. and V.L. Braciale, "Antigen presentation: structural themes and functional variations," *Immunol. Today* 12:124-129 (1991).
Kovacsovics-Bankowski, M. and K.L. Rock, "A Phagosome-to-Cytosol Pathway for Exogenous Antigens Presented on MHC Class I Molecules," *Science* 267:243-246 (1995).
Marchand, M. et al., "Tumor regression responses in melanoma patients treated with a peptide encoded by gene MAGE-3," *Int. J. Cancer* 63:883-885 (1995).
Oettgen, H.F. and L.J. Old, "Chapter 6: The History of Cancer Immunotherapy," In: *Biologic Therapy of Cancer*, DeVita, V.T. et al., eds., J.B. Lippincott Company, Philadelphia, PA, pp. 87-119 (1991).

(Continued)

*Primary Examiner*—David Saunders
(74) *Attorney, Agent, or Firm*—Sterne, Kessler, Goldstein & Fox P.L.L.C.

(57) ABSTRACT

Pharmaceutical composition containing at least one peptide or protein (fragment) with an immunomodulatory activity together with an adjuvant. The peptide is derived from a pathogenic agent or a tumour antigen. The adjuvant is capable of increasing the binding of the peptide to the cells of the individual to be treated or of increasing the entry of the peptide into the cells and strengthening the immunomodulatory activity of the peptide. Preferred adjuvants are basic polyamino acids such as polyarginine or polylysine, optionally conjugated with a cellular ligand such as a carbohydrate group or transferrin. The composition is particularly intended for use as a vaccine, e.g. as a tumour vaccine.

32 Claims, 24 Drawing Sheets

OTHER PUBLICATIONS

Porgador, A. and E. Gilboa, "Bone Marrow-generated Dendritic Cells Pulsed with a Class I-restricted Peptide Are Potent Inducers of Cytotoxic T Lymphocytes," *J. Exp. Med. 182*:255-260 (1995).

Ryser, H. J.-P. and R. Hancock, "Histones and Basic Polyamino Acids Stimualate the Uptake of Albumin by Tumor Cells in Culture," *Science 150*:501-503 (1965).

Ryser, H. J.-P. and W.-C. Shen, "Conjugation of methotrexate to poly(L—lysine) increases drug transport and overcomes drug resistance in cultured cells," *Proc. Natl. Acad. Sci. USA 75*:3867-3870 (1978).

Schmidt, W. et al., "Transloading of tumor cells with foreign major histocompatability complex class I peptide ligand: A novel general strategy for the generation of potent cancer vaccines," *Proc. Natl. Acad. Sci. USA 93*:9759-9763 (Sep. 1996).

Shen, W.-C. and H. J.-P. Ryser, "Poly(L—Lysine) has different membrane transport and drug-carrier properties when complexed with heparin," *Proc. Natl. Acad. Sci. USA 78*:7589-7593 (1981).

Stuber, G. et al., "Identification of wild-type and mutant p53 peptides binding to HLA-A2 assessed by a peptide Loading-deficient cell line assay and a novel major histocompatibility complex class I peptide binding assay," *Eur. J. Immunol. 24*:765-768 (1994).

Tykocinski, M.L. et al., "Antigen-Presenting Cell Engineering," *Amer. J. Pathology 148*:1-16 (Jan. 1996).

York, I.A. and K.L. Rock, "Antigen Processing and Presentation by the Class I Major Histocompatibility Complex," *Annu. Rev. Immunol. 14*:369-396 (Jan. 1996).

Young, J.W. and K. Inaba, "Dendritic Cells as Adjuvants for Class I Major Histocompatibility Complex-restricted Antitumor Immunity," *J. Exp. Med. 183*:7-11 (Jan. 1996).

Zatloukal, K. et al., "Somatic gene therapy for cancer: the utility of transferrinfection in generating 'tumor vaccines'," *Gene 135*:199-207 (1993).

Dialog 351, Derwent, WPI Accession No. 97-298108, English language abstract of WO 97/19169 (Document AN2).

Dialog 351, Derwent, WPI Accession No. 97-434862, English language abstract of WO 97/30721 (Document AO2).

* cited by examiner

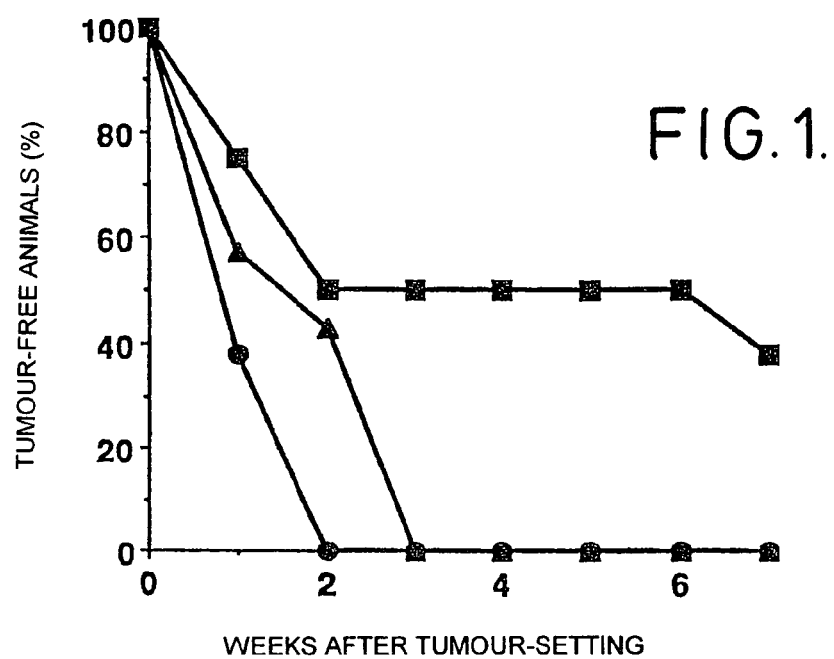

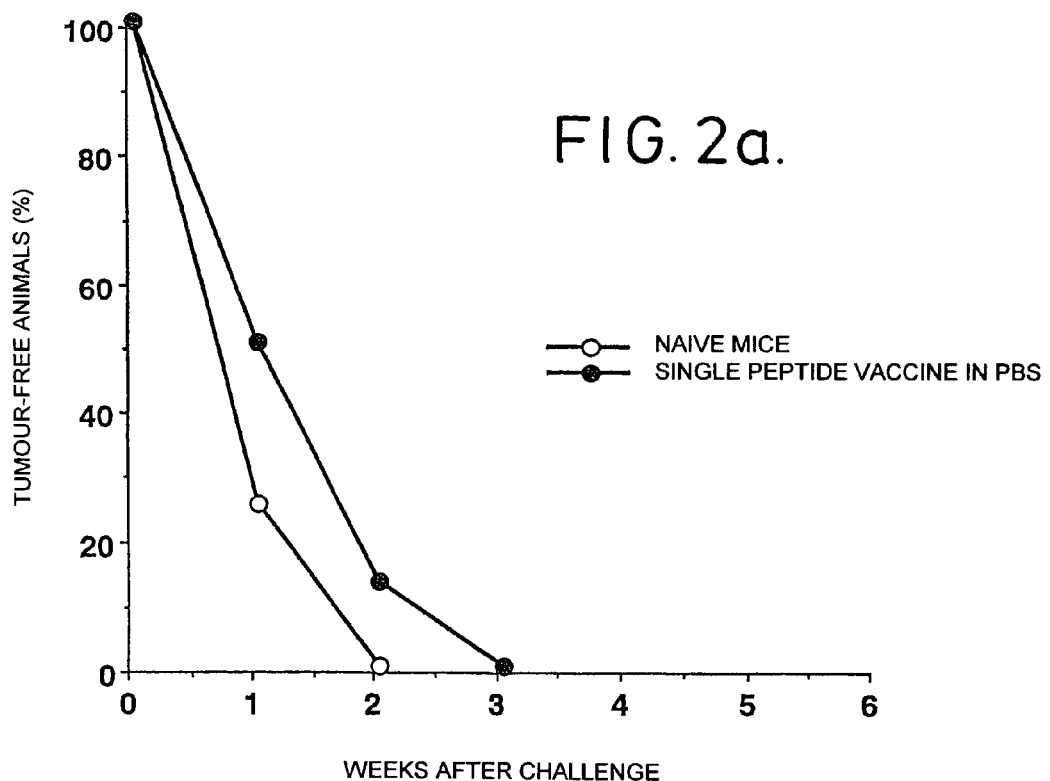

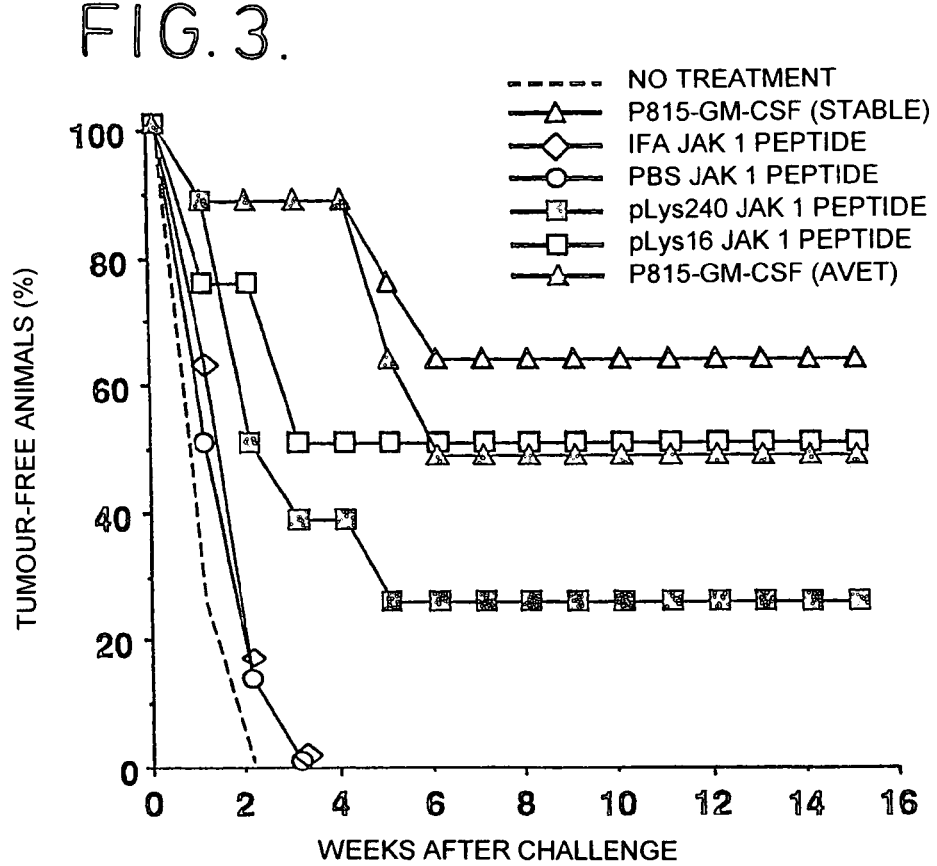

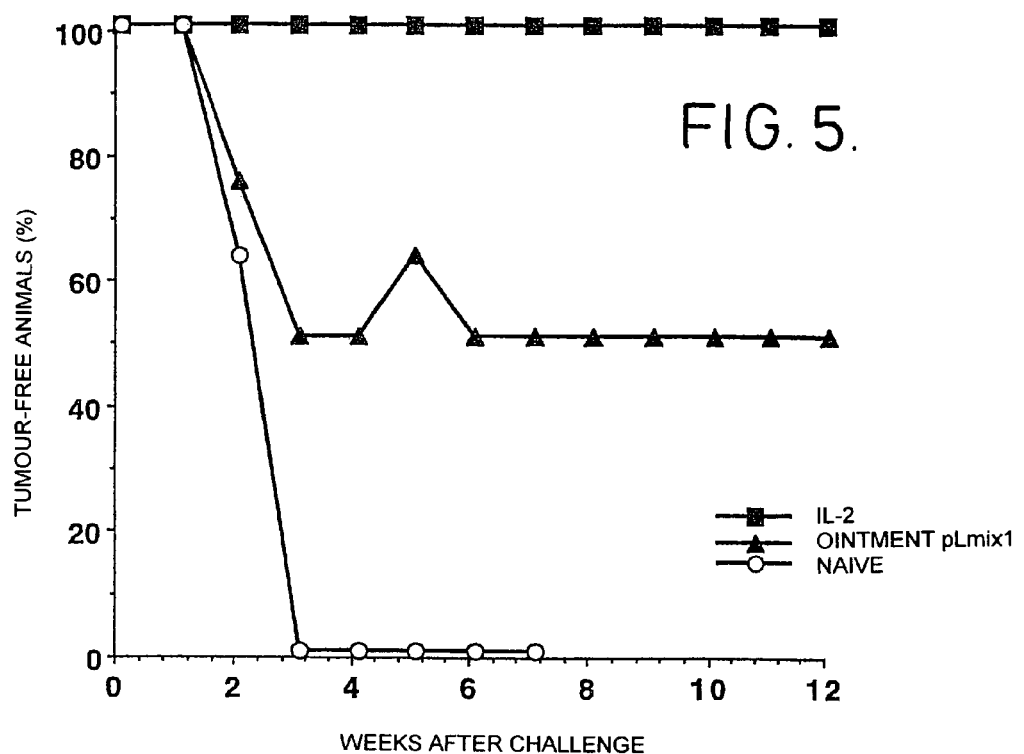

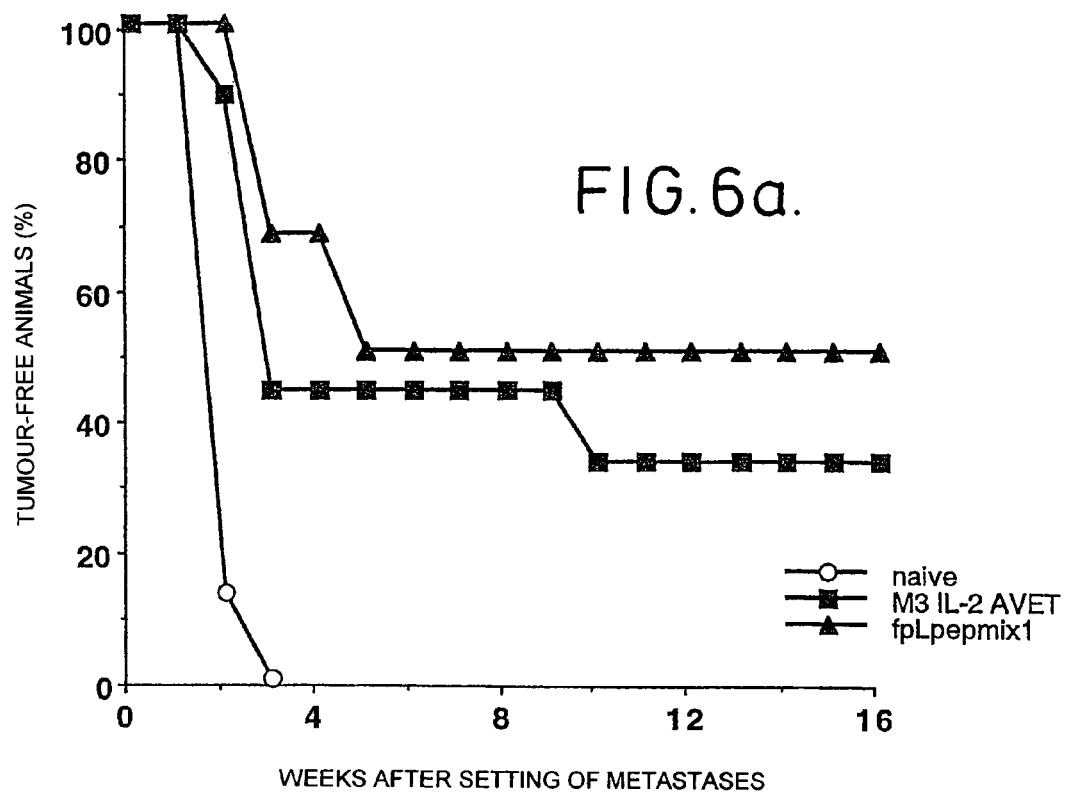

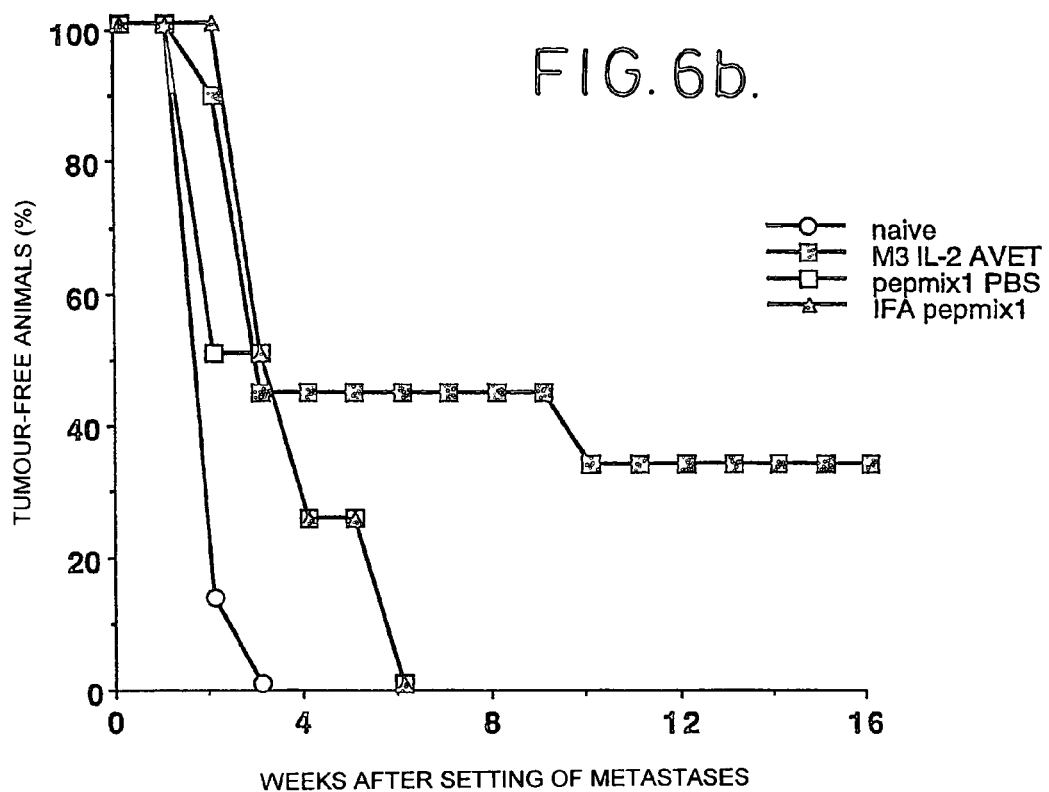

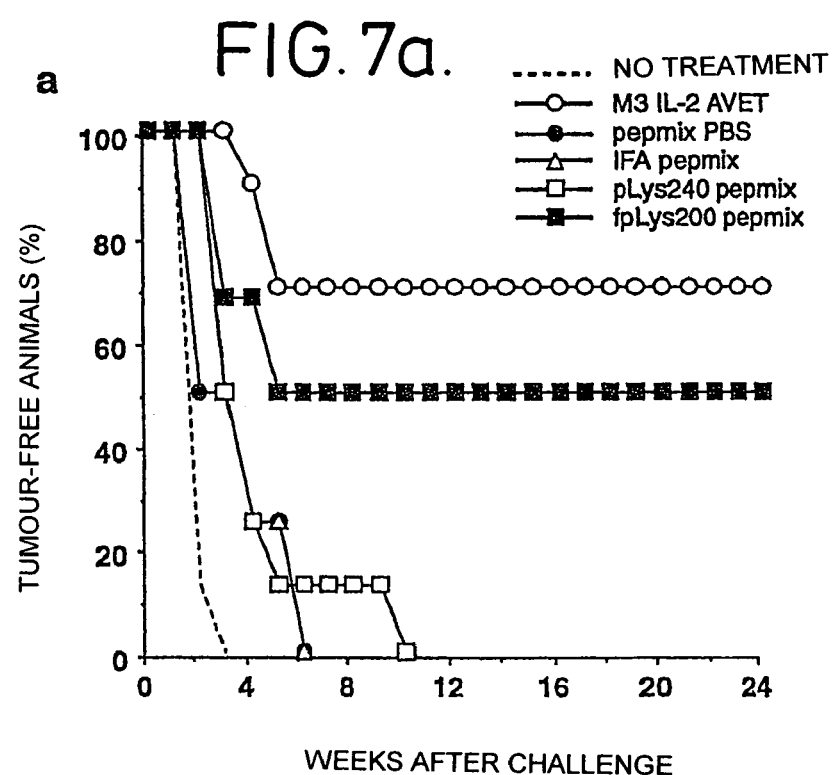

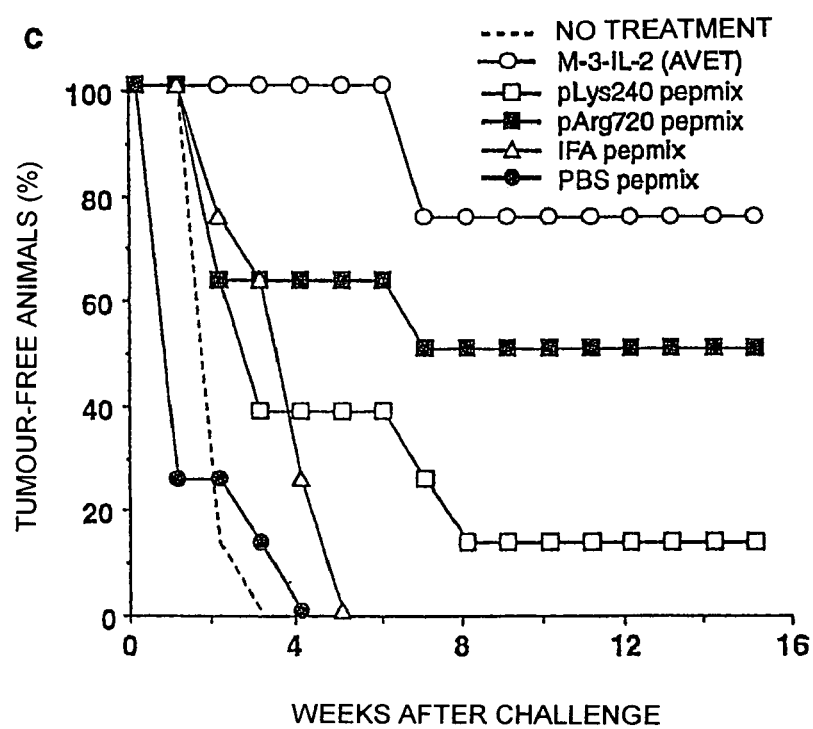

FIG. 11.
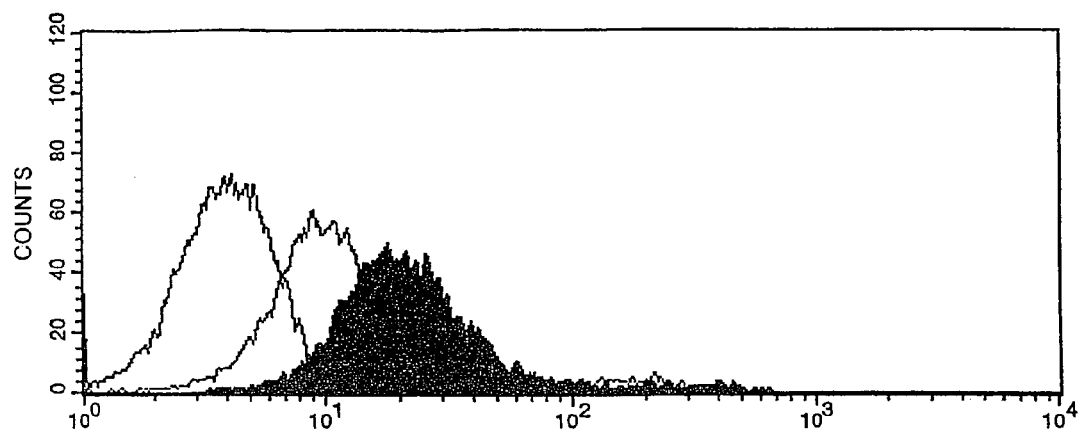
LOG FLUORESCENCE
POLYLYSINE
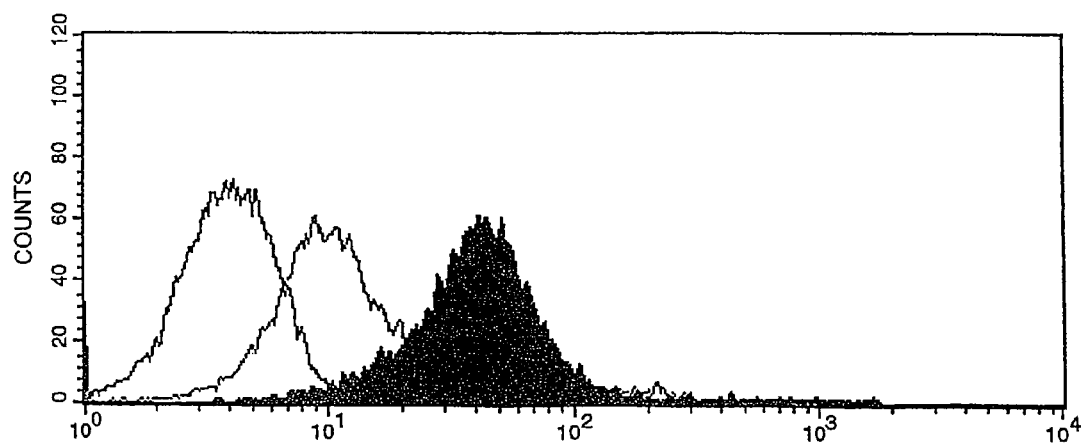
LOG FLUORESCENCE
POLYARGININE FIG. 12.
A    POLYARGININE
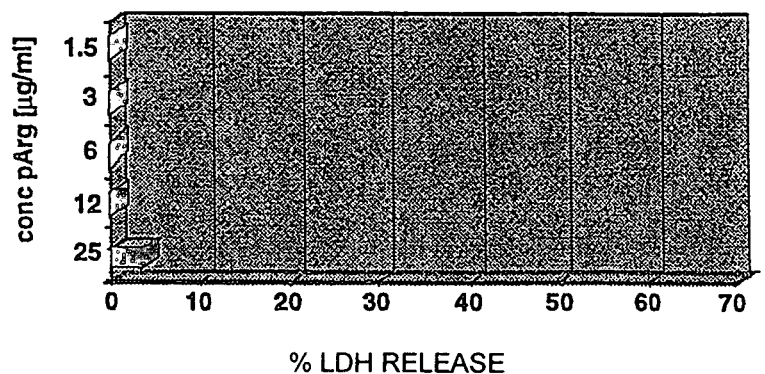
B    POLYLYSINE
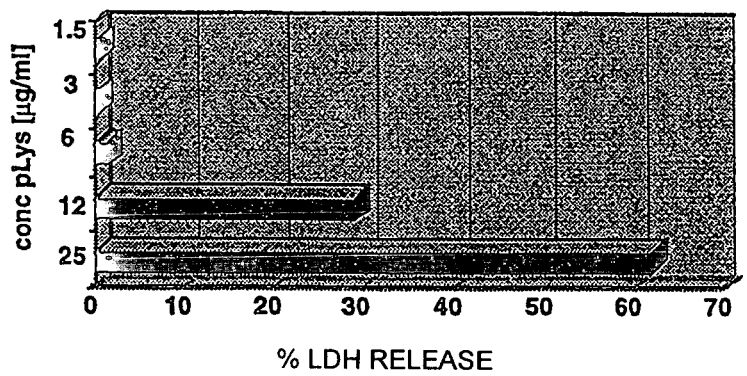

FIG. 14.
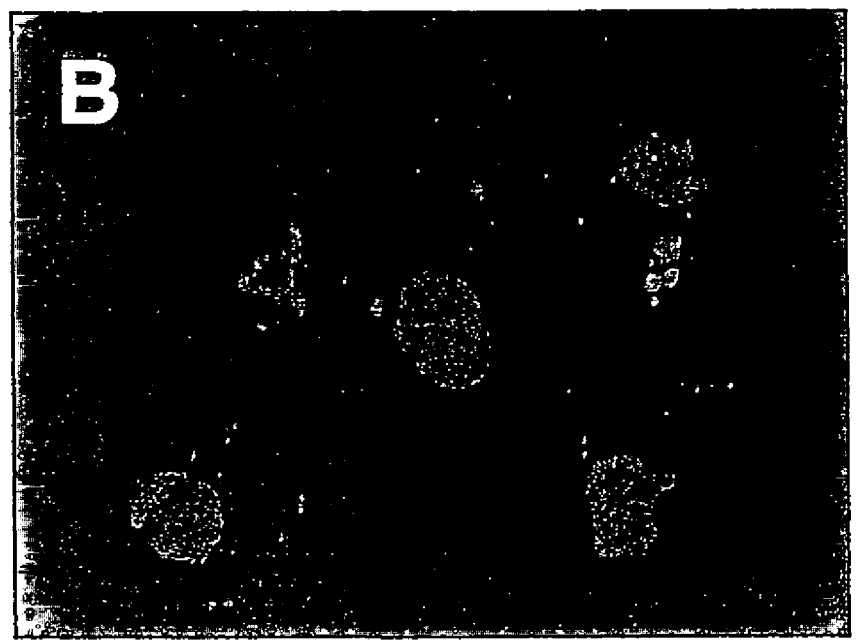

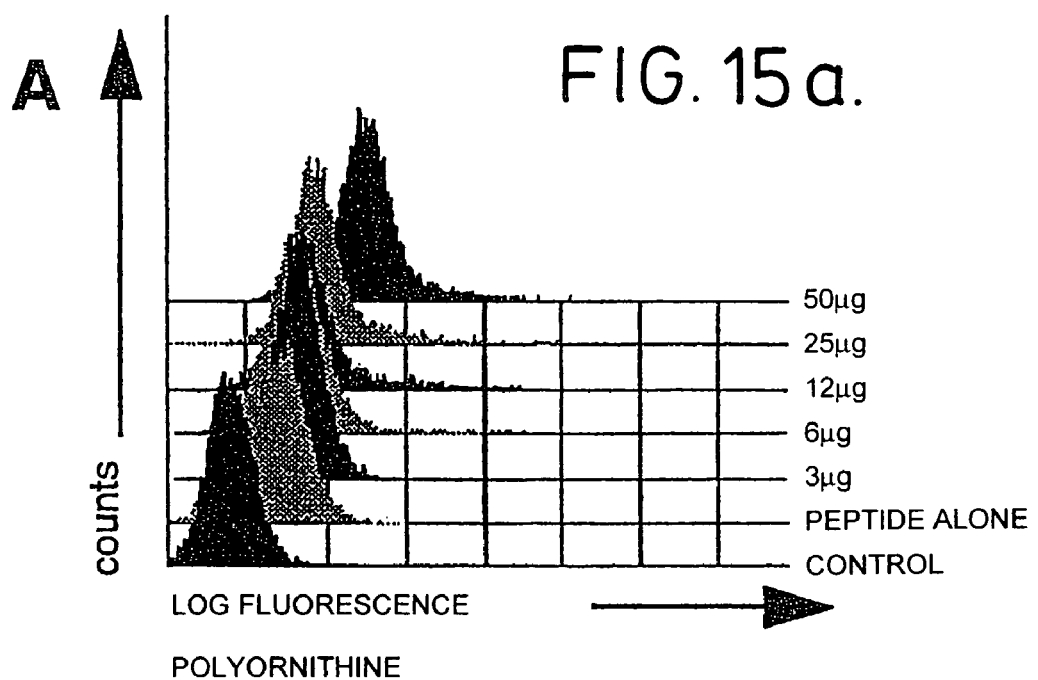
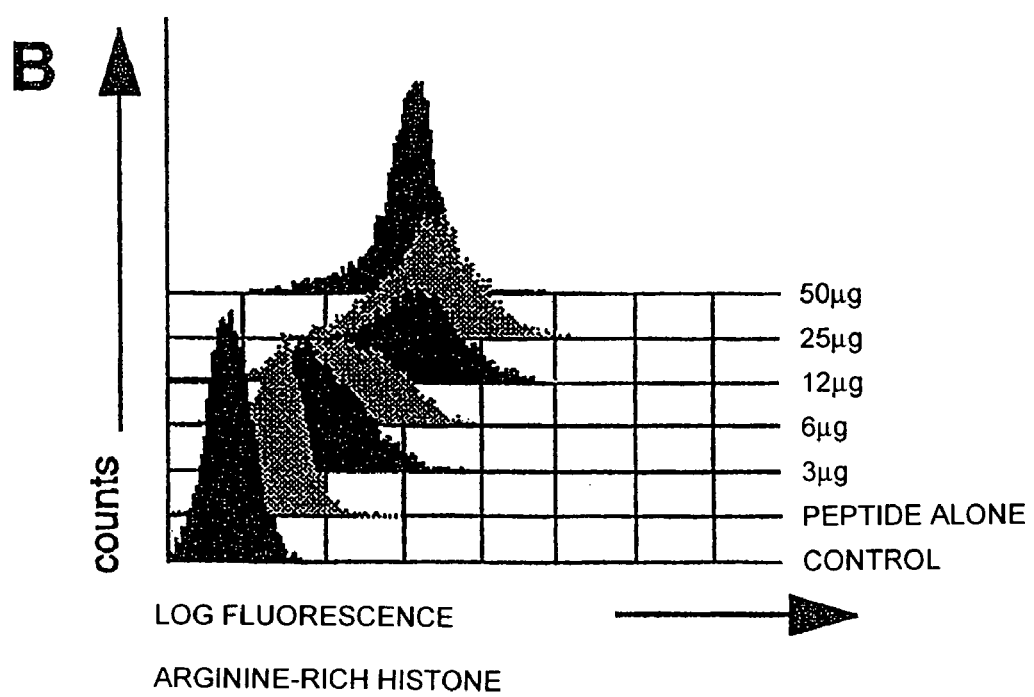
FIG. 15a.

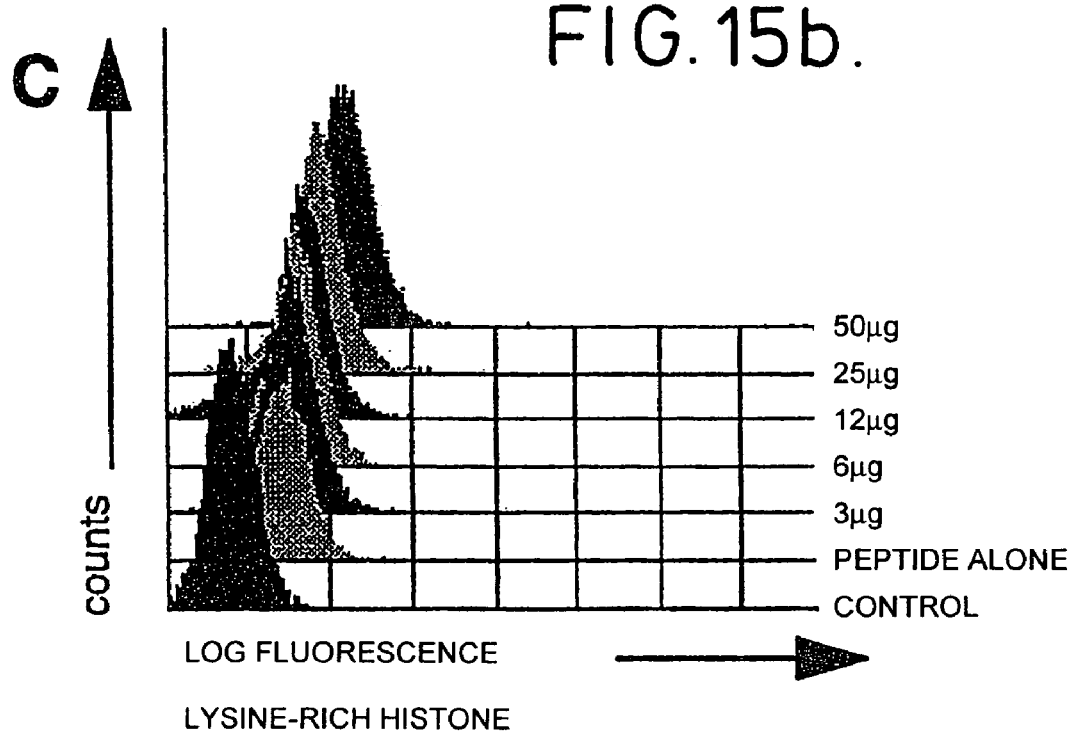
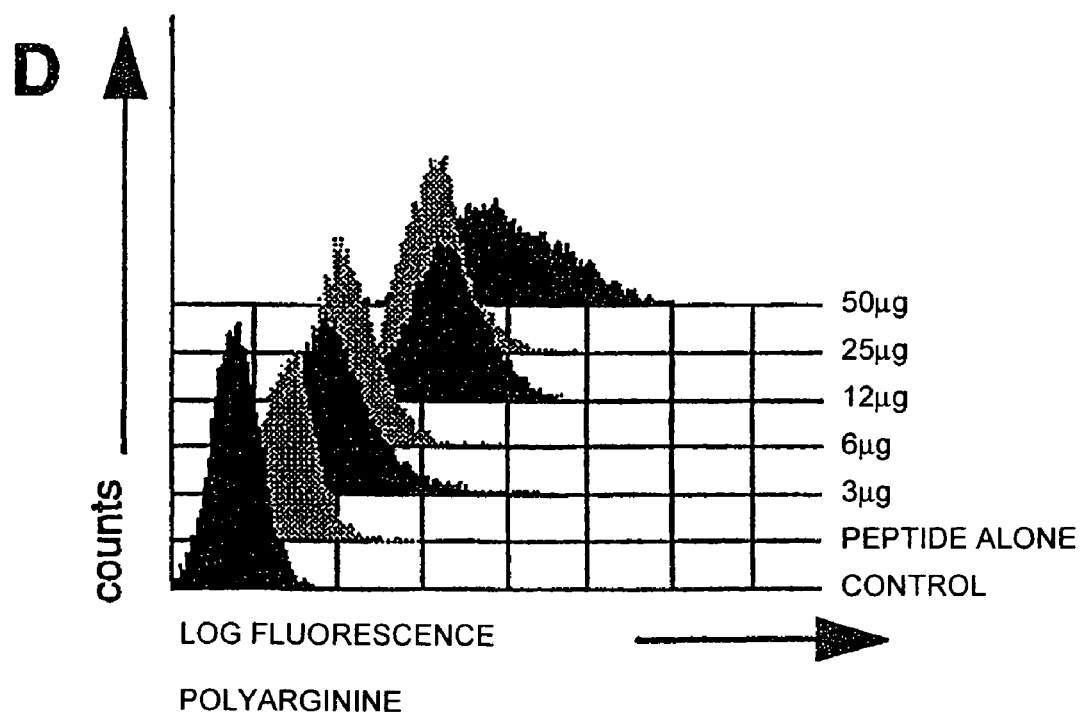
FIG. 15b.

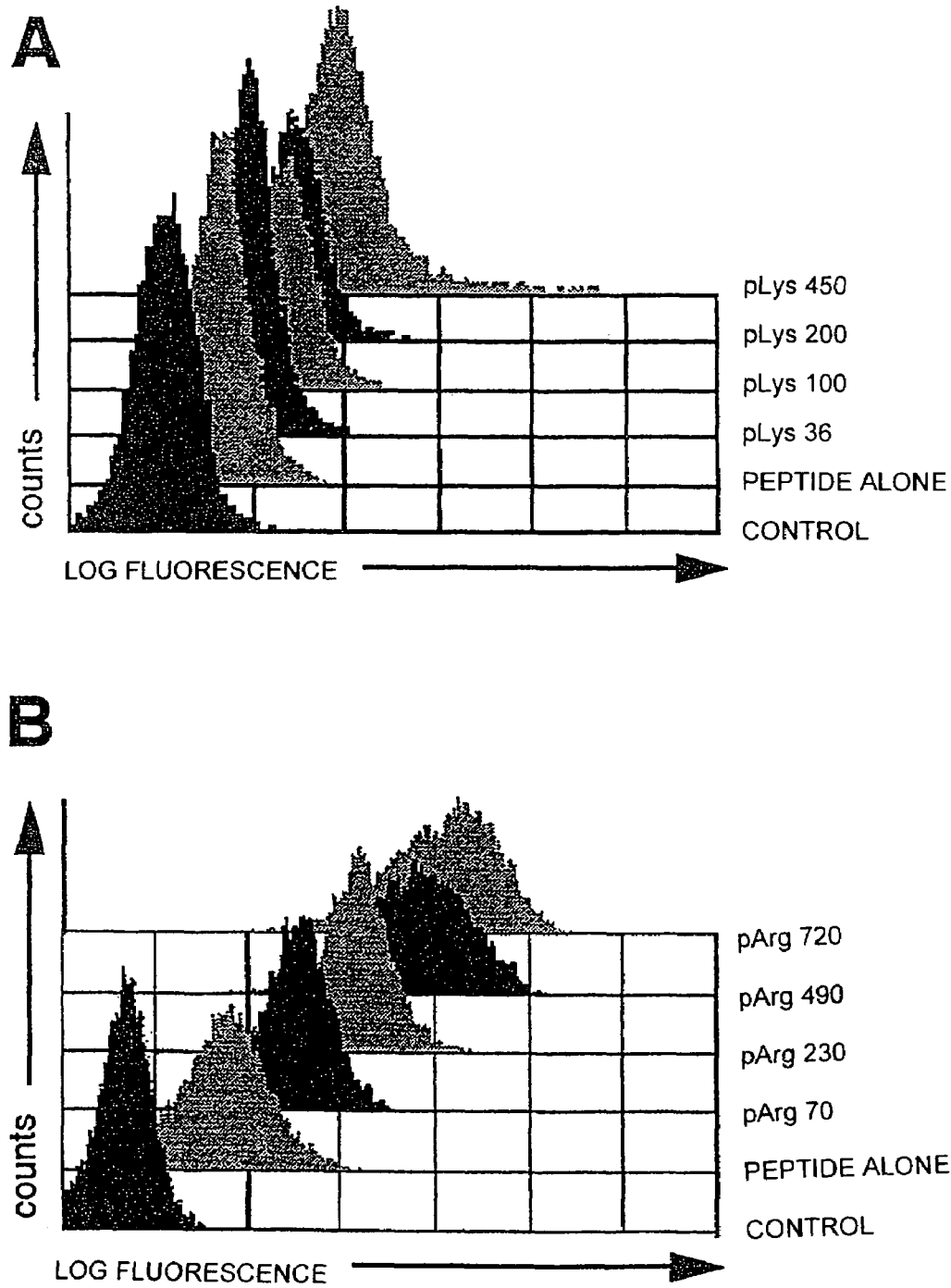

PHARMACEUTICAL COMPOSITION FOR IMMUNOMODULATION BASED ON PEPTIDES AND ADJUVANTS

This application claims the benefit of priority of the filing date of German Patent Application No. 196 07 044.09, filed Feb. 24, 1996; German Patent Application No. 196 38 313.7, filed Sep. 19, 1996; and German Patent Application No. 196 48 687.4, filed Nov. 25, 1996; the disclosures of each of which are incorporated by reference herein in their entirety.

The invention relates to the field of immunomodulation.

The invention is a development of a therapeutic vaccine based on tumour cells which is essentially dependent on the following conditions: there are qualitative or quantitative differences between tumour cells and normal cells; the immune system is fundamentally capable of recognising these differences; the immune system can be stimulated—by active specific immunisation with vaccines—to recognise tumour cells by means of these differences and cause them to be rejected.

In order to achieve an anti-tumour response, at least two conditions must be satisfied: firstly, the tumour cells must express antigens which do not occur on normal cells, or occur only to the extent that the immune system can distinguish qualitatively between normal and tumour tissue. Secondly, the immune system must be activated accordingly in order to react to these antigens. A serious obstacle in the immune therapy of tumours is their low immunogenicity, particularly in humans.

Recently, tumour-associated and tumour-specific antigens have been discovered which constitute such neo-epitopes and thus ought to constitute potential targets for an attack by the immune system. The fact that the immune system nevertheless does not succeed in eliminating the tumours which express these neo-epitopes would then obviously not be due to the absence of neo-epitopes but due to the fact that the immunological response to these neo-antigens is inadequate.

For immunotherapy of cancer on a cellular basis, two general strategies have been developed: on the one hand, adoptive immunotherapy which makes use of the in vitro expansion of tumour-reactive T-lymphocytes and their reintroduction into the patient; on the other hand, active immunotherapy which uses tumour cells in the expectation that this will give rise to either new or more powerful immune responses to tumour antigens, leading to a systemic tumour response.

Tumour vaccines based on active immunotherapy have been prepared in various ways; one example consists of irradiated tumour cells mixed with immunostimulant adjuvants such as *Corynebacterium parvum* or Bacillus Calmette Guerin (BCG) in order to provoke immune reactions against tumour antigens (Oettgen and Old, 1991).

In recent years, in particular, genetically modified tumour cells have been used for active immunotherapy against cancer. A survey of these different approaches in which tumour cells are alienised for more powerful immunogenicity by the incorporation of various genes is provided by Zatloukal et al., 1993. One of the strategies used hitherto uses tumour cells which are genetically modified in order to produce cytokines.

The identification and isolation of tumour antigens and tumour-associated antigens (TAs) or peptides derived therefrom, (e.g. as described by Wölfel et al., 1994 a) and 1994 b); Carrel et al., 1993, Lehmann et al., 1989, Tibbets et al., 1993, or in the published International Applications WO 92/20356, WO 94/05304, WO 94/23031, WO 95/00159) was the prerequisite for another strategy using tumour antigens as immunogens for tumour vaccines, both in the form of proteins and in the form of peptides. From the work of Boon et al., 1992; Boon et al., 1994; Boon et al., 1995; van Peel et al., 1995; Van der Eynde, 1995, it was known that malignant melanomas present tumour antigen-derived peptides in the MHC-I context. However, a tumour vaccine in the form of tumour antigens as such is not sufficiently immunogenic to trigger a cellular immune response which would be necessary to eliminate tumour cells carrying tumour antigen (Marchand et al., 1995). To ensure that antigen-presenting cells (APCs) present defined peptide antigens on their surface it was proposed to "pulse" the peptides, but this resulted in inefficient loading of the cells with peptides (Tykocinski et al., 1996); it was also shown that the co-administration of adjuvants had only limited success in intensifying the immune response (Oettgen and Old, 1991).

A third strategy for active immunotherapy in order to increase the efficacy of tumour vaccines is based on xenogenised (alienised) autologous tumour cells. This concept is based on the assumption that the immune system reacts to tumour cells which express a foreign protein and that, in the course of this reaction, an immune response is also provoked against those tumour antigens which are presented by the tumour cells of the vaccine.

A central role is played in the regulation of the specific immune response by a trimolecular complex consisting of the components of T-cell-antigen receptor, MHC (Major Histocompatibility Complex) molecule and the ligand thereof which is a peptide fragment derived from a protein.

MHC molecules (or the corresponding human molecules, the HLAs) are peptide receptors which allow the binding of numerous different ligands, with stringent specificity. The prerequisite for this is provided by allele-specific peptide motifs which have the following specificity criteria: the peptides have a defined length, depending on the MHC haplotype, this length generally being from eight to ten amino acid groups in the MHC-I haplotype. Typically, two of the amino acid positions are so-called "anchors" which can only be occupied by a single amino acid or by amino acid groups with closely related side chains. The exact position of the anchor amino acids in the peptide and the requirements made on their properties vary with the MHC-haplotypes. The C-terminus of the peptide ligands is frequently an aliphatic or a charged group. Such MHC-I-peptide-ligand motifs have hitherto been known, inter alia, for H-2 $K^d$, $K^b$, $K^k$, $K^{kml}$, $D^b$, HLA-A*0201, A*0205 and B*2705 haplotypes.

Within the scope of the protein conversion inside the cell, regular, degenerate and foreign gene products, e.g. viral proteins or tumour antigens, are broken down into small peptides; some of them constitute potential ligands for MHC molecules. This provides the prerequisite for their presentation by MHC-molecules and, as a result, the triggering of a cellular immune response, although it has not yet been clearly explained how the peptides are produced as MHC ligands in the cell. Foreign or alienised proteins and the fragments thereof may also be recognised, bound and eliminated by immunoglobulins which constitute the humoral immune response. This is also true of all tumour antigens: using the example of tumour associated antigens MUC1, CEA and HER2/neu it has been shown that immunoglobulins which have specificity for these proteins are able to recognise and kill the protein-carrying cells. In order to trigger a tumour antigen-specific humoral immune response, therefore, various forms of MUC1 and CEA were tried out as immunogens (e.g. in recombinant poxvectors; Bronte et al., J. Immunol. 154:5282 1995) in animal models and preliminary clinical trials.

Within the scope of the invention, some ideas were pursued which had come up in the development of a cellular tumour vaccine: whereas non-malignant normal body cells are tolerated by the immune system, the body reacts to a normal cell by means of an immune response if this cell synthesises proteins foreign to the body, e.g. as the result of a viral infection. The reason for this is that the MHC molecules present foreign peptides which originate from the foreign proteins. Consequently, the immune system registers that something undesirable and alien has happened to this cell. APCs (these include macrophages, dendritic cells, Langerhans cells, B-cells and possibly the recently discovered biphenotypic cells which have the properties of both B-cells and also macrophages; Tykocinski et al., 1996) are activated, a new specific immunity is generated and the cell is eliminated.

Tumour cells admittedly contain the tumour-specific tumour antigens in question but are ineffective vaccines as such, because they are ignored by the immune system as the result of their low immunogenicity. If a tumour cell were to be charged not with a foreign protein but with a foreign peptide, in addition to the foreign peptides the cell's own tumour antigens will be recognised as foreign by this cell. By alienisation with a peptide the intention is to direct the cellular immune response triggered by the foreign peptides against the tumour antigens.

The reason for the low immunogenicity of tumour cells may be a problem not of quality but of quantity. For a peptide derived from a tumour antigen, this may mean that it is indeed presented by MHC molecules but in a concentration which is too low to trigger a cellular tumour-specific immune response. An increase in the number of tumour-specific peptides on the tumour cell should thus also result in alienisation of the tumour cell, resulting in the triggering of a cellular immune response. It has been proposed to present the tumour antigen or the peptide derived from it on the cell surface by transfecting it with a DNA coding for the protein or peptide in question, as described in International Publications WO 92/20356, WO 94/05304, WO 94/23031 and WO 95/00159.

German Patent Application P 195 43 649.0 discloses a cellular vaccine which contains as active component tumour cells charged with one or more peptides so that the tumour cells in context with the peptides are recognised as foreign by the patient's immune system and trigger a cellular immune response. An essential feature of the peptides is that they are ligands for the MHC-haplotype of the patient. The peptides are therefore recognised as foreign by the patient's immune system because they may be, on the one hand, "foreign peptides" or "xenopeptides", i.e. they are different from peptides derived from proteins which are expressed by the patient's tumour cells. Another category of peptides is derived from tumour antigens expressed by the patient's cells. These bring about an increase in immunogenicity by the fact that they are present on the tumour cells of the vaccine in a concentration which is greater than the concentration of the same peptide on the patient's tumour cells.

The aim of the present invention was to provide a new pharmaceutical composition having an immunomodulatory activity, particularly a vaccine.

In furtherance of the concept of the cellular vaccines disclosed in German Patent Application P 195 43 649.0, a pharmaceutical composition has been developed within the scope of the present invention which contains peptides having an immunomodulatory effect not in context with cells but together with an adjuvant, in order to trigger or intensify a cellular and/or humoral, preferably systemic, immune response to pathogens or an anti-tumour response or to bring about tolerance to proteins with an autoimmune activity.

It has been found that, surprisingly, certain adjuvants, e.g. polycations, which were first shown back in 1965 to be capable of increasing the transfer of proteins into cells (Ryser et al., 1965; Ryser et al., 1978; Shen et al., 1981), increase the immunogenicity of peptides.

The invention relates to a pharmaceutical composition containing one or more peptides, proteins or protein fragments with an immunomodulatory effect together with an adjuvant. The composition is characterised in that the adjuvant has the ability to increase the binding of the peptide or protein or protein fragment to cells of the individual to be treated or to promote the entry of the peptide into cells and bring about an increase in the immunomodulatory effect of the peptide or protein or protein fragment.

In general, for simplicity's sake, examples of the peptides, proteins or protein fragments with an immunomodulatory effect as mentioned above will henceforth be referred to as "peptides". The term "peptide", when not referring specifically to the ligand, may also indicate larger protein fragments or proteins from which the peptide is derived, or a cellular breakdown product.

The term "immunomodulatory effect" denotes, on the one hand, the triggering or intensification of a cellular and/or humoral, preferably systemic, immune reaction. In this embodiment, the pharmaceutical composition according to the invention acts as a vaccine.

In a preferred embodiment the peptides are ligands for at least one MHC molecule expressed by the individual to be treated.

The human MHC molecules are hereinafter also referred to as HLA (Human Leucocyte Antigen) in accordance with international conventions.

The term "cellular immune response" denotes in particular the cytotoxic T-cell immunity which, as a result of the generation of cytotoxic CD8-positive T-cells and CD4-positive helper-T-cells, brings about destruction of the tumour cells or of the cells attacked by the pathogen.

The expression "humoral immune response" denotes the production of immunoglobulins which selectively recognise tumour cells or structures derived from pathogens and consequently, together with other systems such as, for example, complement, ADCC (antibody dependent cytotoxicity) or phagocytosis, bring about the destruction of these tumour cells or the cells attacked by the pathogenic agents.

The peptide contained in the vaccine is derived from an antigen, or, in the case of proteins, is an antigen against which a cellular and/or humoral immune response is to be triggered. This ensures that T-cells or other cytotoxic effector cells which recognise the disease-causing agent or the tumour cells which contain the antigen, and/or antibodies are generated.

For immunisation against pathogenic agents of disease such as bacteria, viruses and parasites, proteins or peptides are used which constitute a protein of the pathogen or pathogens in question or are derived therefrom. Particularly suitable are proteins which are unaffected by the high general mutation rate of these pathogens. Published examples include HPV16/17 (Human Papilloma Virus; Feltkamp et al., 1995), Hepatitis B Virus Core Antigen (Vitiello et al., 1995), *Plasmodium Bergheii* (Widmann et al., 1992), influenza virus nucleoprotein and hepatitis C virus.

In one embodiment of the invention, the protein, with a view to triggering an anti-tumour response, or a tumour antigen or the peptide is derived from a tumour antigen and the pharmaceutical composition is used as a tumour vaccine. In this case, when the vaccine is used therapeutically, the peptide is derived from a tumour antigen which is expressed by the patient's tumour cells. These tumour antigens are, for example, those which are expressed by the patient in a concentration which is too low, with the result that the tumour cells are not recognised as foreign.

The tumour antigens of the patient can be determined in the course of drawing up the diagnosis and treatment plan by standard methods: tumour antigens can easily be detected by immunohistochemistry using antibodies. If the tumour antigens are enzymes, e.g. tyrosinases, they can be detected by enzyme assays. In the case of tumour antigens with a known sequence, the RT-PCR method can be used (Boon, T., et al., 1994; Coulie, P. G., et al., 1994; Weynants, P., et al., 1994). Other methods of detection are assays based on CTLs with specificity for the tumour antigen which is to be detected. These assays have been described, for example, by Herin et al., 1987; Coulie et al., 1993; Cox et al., 1994; Rivoltini et al., 1995; Kawakami et al., 1995; and have been described in WO 94/14459; these references also disclose various tumour antigens and peptide epitopes derived therefrom which are suitable within the scope of the present invention. Examples of suitable tumour antigens are also given in the summarising articles published recently by Rosenberg, 1996, and Henderson and Finn, 1996. Regarding the tumour antigens which can be used the present invention is not subject to any limitations; some examples of known tumour antigens and peptides derive therefrom which may be used for the purposes of the invention are given in the Table.

A tumour vaccine containing a tumour antigen or peptides derived from a tumour antigen may be used not only therapeutically but also prophylactically. For prophylactic use, it is preferable to use a mixture of peptides derived from representatives of commonly occurring tumour antigens. When the tumour vaccines according to the invention are used therapeutically, one or more peptides are used, which can be expected to be contained in tumour antigens of the patient.

The tumour vaccine according to the invention has the advantage, over a cellular vaccine based on autologous tumour cells, that it is therapeutically useful even for patients at a relatively early stage (stage I and II) of the disease, who have insufficient tumour cells to produce a cell vaccine.

In a preferred embodiment of the invention the peptide is matched to the MHC-I- or MHC-II-subtype of the patient to be vaccinated, with a view to triggering a cellular immune response; the peptide thus has a sequence or contains a sequence which ensures that it binds to an MHC-molecule.

In another embodiment, the pharmaceutical composition in its form as a tumour vaccine also contains a polypeptide with an immunostimulant effect, particularly a cytokine. In a preferred embodiment of the invention the cytokine used is interleukin 2 (IL-2) or GM-CSF, e.g. in a dosage of about 1000 units; other examples of cytokines are IL-4, IL-12, IFN-α, IFN-β, IFN-γ, IFN-ω, TNF-α and combinations thereof, e.g. IL-2+IFN-γ, IL-2+IL-4, IL-2+TNF-α or TNF-α+IFN-γ.

In one embodiment of the invention the pharmaceutical composition serves to confer tolerance to proteins or the fragments thereof which trigger autoimmune-induced diseases, i.e. for the treatment of autoimmune diseases. The peptides used in this embodiment of the invention are derived from proteins which cause autoimmune diseases.

In contrast to the application of the invention as a tumour vaccine or as a vaccine against pathogenic agents in which the peptides substantially match a portion of the original protein (tumour antigen or protein of the pathogen) to the extent that the peptide is recognised as the "original antigen", when the invention is applied to the treatment of autoimmune diseases, peptides are used, inter alia, which differ from the amino acid sequence of the original protein in some crucial respects. These peptides do indeed bind to the MHC-molecule as a result of their anchor positions but they have mutations in their sequence which cause these peptides to act as antagonists which switch off the activated specific T-cells again (Kersh and Allen, 1996).

Suitable peptide antagonists are both "natural" antagonists which were discovered in viruses (Bertoletti et al., 1994) and also antagonists found by systematic searching, e.g. by screening peptide libraries. Examples of peptide antagonists are peptides which are able to switch off T-cells which are specific for myelin basic protein; these were tested for their effectiveness in animal experiments (Brocke et al., 1996).

A peptide which is supposed to trigger a cellular immune response must be capable of binding to an MHC-molecule. In order that the immune response is triggered in the patient, the individual to be treated must therefore have a corresponding HLA-molecule in their repertoire. The determination of the HLA-subtype of the patient thus constitutes one of the most important prerequisites for effective administration of a peptide to this patient, in terms of obtaining a cellular immune response.

The HLA subtype of the patient can be detected using standard methods such as the micro-lymphotoxicity test (Practical Immunol., 1989). This test is based on the principle of mixing lymphocytes isolated from the patient's blood first with antiserum or a monoclonal antibody against a specific HLA molecule in the presence of rabbit complement (C). Positive cells are lysed and absorb an indicator dye, whereas undamaged cells remain unstained.

RT-PCR can also be used to determine the HLA-I or HLA-II-haplotype of a patient (Curr. Prot. Mol. Biol. Chapters 2 and 15). In order to do this, blood is taken from the patient and RNA is isolated from it. This RNA is subjected first to reverse transcription, resulting in the formation of cDNA from the patient. The cDNA is used as a matrix for the polymerase chain reaction with primer pairs which specifically bring about the amplification of a DNA fragment which represents a certain HLA-haplotype. If after agarose gel electrophoresis a DNA band appears, the patient expresses the corresponding HLA molecule. If the band does not appear, the patient is negative for it.

The definition of a peptide used according to the invention by means of an HLA-molecule defines them in terms of their anchor amino acids and their length; defined anchor positions and length ensure that the peptide fits into the peptide binding fork of the HLA molecule in question. This means that the immune system will be stimulated and a cellular immune reaction will be provoked against the tumour cells of the patient, if a peptide derived from a tumour antigen is used.

Peptides which are suitable for the purposes of the present invention are available in a wide range. Their sequence may be derived from naturally occurring immunogenic proteins or the cellular breakdown products thereof, e.g. viral or bacterial peptides, or from tumour antigens, or they may be antagonists to peptides derived from proteins which induce autoimmune diseases.

Suitable peptides may be selected, for example, on the basis of peptide sequences known from the literature.

With a view to triggering a cellular immune response, the peptides may be defined, e.g. by means of the peptides described by Rammensee et al., 1993, Rammensee et al., 1995, Falk et al., 1991, for the different HLA motifs, peptides derived from immunogenic proteins of various origins, which fit into the binding forks of the molecules of the various HLA-subtypes. For peptides which have a partial sequence of a protein with an immunogenic activity, it is possible to establish which peptides are suitable candidates by means of the polypeptide sequences already known or possibly still to be established, by sequence comparison taking account of the HLA-specific requirements. Examples of suitable peptides are found, for example, in Rammensee et al., 1993, Falk et al., 1991, and Rammensee, 1995 and in WO 91/09869 (HIV peptides); peptides derived from tumour antigens are described, inter alia, in the published International Patent Applications WO 95/00159 and WO 94/05304. Reference is hereby made to the disclosure of these references and the Articles cited therein in connection with peptides. Preferred candidates are the peptides whose immunogenicity has already been demonstrated, i.e. peptides derived from known immunogens such as viral or bacterial proteins.

Instead of using the original peptides which fit into the binding forks of MHC-I or MHC-II molecules, i.e. peptides which are derived unchanged from natural proteins, it is possible to carry out variations as required, using the minimum requirements regarding anchor positions and lengths, specified on the basis of the original peptide sequence, provided that these variations not only do not impair but preferably enhance the effective immunogenicity of the peptide made up of its binding affinity to the MHC molecule and its ability to stimulate T-cell receptors. In this case, therefore, synthetic peptides are used according to the invention which are designed in accordance with the requirements regarding binding to an MHC-I molecule. Thus, for example, starting from the $H2-K^2$-ligand Phe Glu Ala Ile Glu Gly Phe Ile (LFEAIEGFI) (SEQ ID NO:1) it is possible to change the amino acids which are not anchor amino acids in such a way as to obtain the peptide of the sequence Phe Phe Ile Gly Ala Leu Glu Glu Ile (FFIGALEEI) (SEQ ID NO:2); moreover, the anchor amino acid Ile at position 9 can be replaced by Leu. The determination of epitopes of MHC-I- or MHC-II-ligands or the variation thereof may be carried out, for example, using the principle described by Rammensee et al., 1995. The length of the peptide preferably corresponds to a minimum sequence of 8 to 10 amino acids required for binding to the MHC-I molecule, together with the necessary anchor amino acids. The MHC-II-binding motif which extends over nine amino acids has a higher degree of degeneration in the anchor positions. Methods have recently been developed, starting from X-ray structural analysis of MHC-II molecules, which permit accurate analysis of the MHC-II binding motifs and, on the basis thereof, variations in the peptide sequence (Rammensee et al., 1995, and the original literature cited therein).

If desired, the peptide may also be lengthened at the C- and/or N-terminus provided that this lengthening does not interfere with the ability to bind the MHC molecule, i.e. that the extended peptide can be processed at cellular level down to the minimum sequence.

In one embodiment of the invention the peptide is negatively charged. In this embodiment, the peptide may be extended with negatively charged amino acids, or negatively charged amino acids may be incorporated in the peptide, preferably at positions which are not essential for the recognition by specific CTLs or as anchor-amino acids, in order to achieve electrostatic binding of the peptide to a polycationic adjuvant such as polylysine.

In one embodiment of the invention the antigen is used not in the form of a peptide but as a protein or protein fragment or as a mixture of proteins or protein fragments.

Within the scope of the present invention, larger protein fragments or whole proteins which are guaranteed to be processed, after the application of the patient's APCs, into peptides which fit the MHC-molecule, are suitable.

The protein is an antigen or tumour antigen from which the fragments obtained after processing are derived. In this embodiment, the adjuvant serves to enable or enhance the charging ("transloading") of cells, particularly APCs such as dendritic cells or macrophages, with the tumour antigen or fragments. Proteins or protein fragments thus absorbed are processed by the cells and can then be presented to the immune effector cells in the MHC context and thus trigger or intensify an immune response (Braciale and Braciale, 1991; Kovacsovics Bankowski and Rock, 1995; York and Rock, 1996).

The embodiment of the invention in which proteins or larger protein fragments are used as antigens has the advantage that there is less dependency on the HLA-type of the patient, as the protein is processed into a number of fragments and there is hence greater variability as to the "fitting form" of the peptides.

If proteins or protein fragments are administered, the identity of the processed end product can be demonstrated by chemical analysis (Edman degradation or mass spectrometry of processed fragments; cf. the summarising article by Rammensee et al., 1995 and the original literature cited therein) or by biological assays (ability of the APCs to stimulate T-cells which are specific for the processed fragments).

In principle, peptide candidates which are suitable for producing a cellular immune response are selected in several stages: generally, the candidates are first tested in a peptide binding test for their binding capacity to an MHC molecule, preferably by series of tests.

One suitable method of investigation is based on the ability of peptides to stabilise empty MHC-molecules, as described for example by Stuber et al., 1994 and McIntyre et al., 1996. The peptide is applied to cells which are capable of expressing the MHC-molecule in question but which do not bind any endogenous peptides in the MHC-context because of a genetic defect. Suitable cell lines of this type are RMA-S (mouse) and T2 (human) and the transfected variants thereof. Then only the MHC-molecules stabilised by the peptide in question are detectable, preferably by means of the FACS analysis based on flow cytometry (Flow Cytometry, 1989; FACS Vantage TM User's Guide, 1994; CELL Quest™ User's Guide, 1994). Stable MHC molecules are detected with a suitable anti-MHC antibody and with a second (e.g. polyclonal) antibody marked with a fluorescent dye, e.g. with FITC (fluorescein isothiocyanate). In the flow, individual cells are excited by a laser of a certain wavelength; the fluorescence emitted is measured and is dependent on the quantity of peptide bound to the cell.

Another method of determining the quantity of peptide bound is the Scatchard blot, as described by Sette et al., 1994. Peptide labelled with $I^{125}$, for example, is used for this and incubated overnight with isolated or recombinantly produced MHC molecules at 4° C. with various defined concentrations of peptide. In order to determine non-specific interaction of the peptide, an excess of unlabelled peptide is added to some of the samples, preventing the non-specific interaction of the labelled peptide. Then the non-specifically bound peptide is removed, e.g. by gel chromatography. The quantity of bound peptide is then determined in a scintillation counter using the radioactivity emitted. The data thus obtained are evaluated using standard methods.

A summary of methods of characterising the MHC/peptide interaction, the analysis of MHC-ligands and peptide-binding assays which may be used within the scope of the present invention is provided by Rammensee et al., 1995.

In a second step, peptide candidates with good binding qualities are tested for their immunogenicity:

The triggering of a cellular immune response can be confirmed by detecting peptide-specific. CTLs, for example in Current Protocols in Immunology, Chapter 3, or in Blomberg et al., 1993. Another indication of the presence of a cellular immune response is provided when, in the absence of T-cells, there is no immune response in an experimental animal (which is achieved by treating the animal with antibodies which deplete the CD4- or CD8-cells) (Current Protocols in Immunology, Chapter 3).

A cellular immune response can also be demonstrated by detecting a "delayed-type hypersensitivity" (DTH) reaction in immunised animals. For this purpose, peptides are injected into the sole of the paw in mice and the swelling at the injected site is measured (Grohman et al., 1995; Puccetti et al., 1994).

The induction of a humoral immune response by peptides which are foreign antigens to the organism or antigens expressed in low concentrations by the organism to be treated, can be determined by detecting specific antibodies in the serum. A suitable method of detecting the antibody level in the serum is enzyme-linked immunoassay (ELISA). The specific antibodies are detected, after binding to the peptide used for immunisation, by means of a staining reaction. An alternative method is Western blot. In this, specific serum antibodies bind to the peptide immobilised on a membrane. Bound antibodies are finally detected again with a staining reaction (reference for both methods: Current Protocols in Immunology. Editors: Coligan et al., 1991).

Particularly after vaccination with foreign antigens, e.g. of viral origin, the formation of antibodies can be expected. However, it cannot be ruled out that specific antibodies may also be formed against mutated or over-expressed peptides derived from cellular tumour antigens. Tumour destruction by such antibodies might take place after antibody binding to tumour cells by other components of the immune system such as, for example, complement, antibody-dependent cytotoxicity (ADCC) or phagocytosis by macrophages (Roitt I. M., Brostoff J., Male D. K. Immunology, Churchill Livingstone).

The triggering of a cellular immune response by peptides which are derived from proteins whose immunogenic activity is unknown may be tested, for example, as described by Rivoltini et al., 1995 or Kawakami et al., 1994a. For this, T-cells are needed which are able to recognise the desired peptide when it is presented by MHC-molecules. In the case of peptides which originate from tumour cells, the corresponding T-cells are obtained from the tumour-infiltrating lymphocytes (TILs) as described by Kawakami et al., 1994b; in the case of foreign peptides, T-cells of this kind are obtained analogously from the peripheral blood. The T-cells are incubated with cell lines such as T2 (Alexander et al., 1989) or RMA-S (Kärre et al., 1986) which have been mixed with the peptide in question, and they lyse them if it is an immunogenic peptide.

Another possible way of testing MHC-binding peptide candidates for their immunogenicity consists in investigating the binding of the peptides to T2 cells. One such test is based on the peculiar nature of T2 cells (Alexander et al., 1989) or RMA-S-cells (Kärre et al., 1986) that they are defective in the TAP peptide transporting mechanism and only present stable MHC-molecules when they are applied to peptides which are presented in the MHC context. T2 cells or RMA-S cells stably transfected with an HLA gene, e.g. with HLA-A1 and/or HLA-A2 genes, are used for the test. If the cells are mixed with peptides which are good HLA ligands, by being presented in the HLA context in such a way as to be recognised as foreign by the immune system, these peptides cause the HLA molecules to appear in significant quantities on the cell surface. Detection of the HLAs on the cell surface, e.g. by means of monoclonal antibodies, makes it possible to identify suitable peptides (Malnati et al., 1995; Sykulev et al., 1994). Here again, a standard peptide known to have a good HLA-binding capacity is appropriately used.

With a view to the broadest possible application of the pharmaceutical composition according to the invention it is preferable to use a mixture of several peptides, each of which is able to bind to another MHC-molecule, preferably to one of two or three of the most commonly occurring MHC-subtypes. A vaccine based on a mixture of peptides which can bind to these haplotypes can be used to cover a wide population of patients.

In one embodiment of the invention, the vaccine may have a number of peptides with different sequences. In this case, the peptides used may differ from one another, on the one hand, in that they bind to different HLA subtypes. In this way, it is possible to detect several or all the HLA subtypes of a patient or of a larger group of patients.

Another, possibly additional, variability with regard to the peptides used may consist in the fact that peptides which bind to a certain HLA subtype differ in their sequence which is not crucial to HLA binding, being derived, for example, from different proteins of the same pathogenic agent or from different pathogens. Variability of this kind can be expected to intensify the stimulation of the immune response or to confer immunity against a variety of pathogens.

The quantity of effective peptide in the composition according to the invention may vary over a wide range. The quantity of peptide depends, inter alia, on the method of administration and the particular formulation used. The quantity of peptide to be administered may be about 1.0 µg to about 5000 µg per dose, generally 1.0 µg to about 1000 µg, particularly about 10 g to about 500 µg. It may be administered once or several times and, if administered several times, preferably at least three times. For therapeutic use, in particular, the peptide may be administered at intervals (e.g. once a week to once a month) over any desired length of time as determined by the specific immune status of the patient or the progress of the disease.

The pharmaceutical composition according to the invention may also be used ex vivo: the principle of possible ex vivo administration consists in cultivating APCs, e.g. dendritic cells, ex vivo, incubating the cell culture with the composition according to the invention and administering the APCs, which now present the peptide in an MHC-context, to the individual who is to be treated. Methods known from the literature may be used for this type of application, as described, for example, by Porgador and Gilboa, 1995; Young and Inabe, 1996.

The adjuvant contained in the composition according to the invention has the property of aiding the entrance of the peptide into the cells or binding the peptide to the cells of the patient and increasing the immunogenicity of the peptide. The adjuvant may, for example, make the membranes of target cells into which the peptide is supposed to penetrate pervious for at least a short time in order to allow the peptide to be conveyed into the cell in this way. It would be advantageous, but not absolutely necessary, for the peptide to be bound to the adjuvant, e.g. by electrostatic interaction between the electronegative peptide and polycationic adjuvant. Entry of the peptide into the cell can also be achieved by the fact that the peptide is able to pass through the cell membrane on the grounds of its spatial closeness thereto, as soon as the adjuvant has made it permeable. The effect of the adjuvant may also be based on the fact that it increases the concentration of the peptide on the cell surface which is critical to its absorption into the cell or that it brings about phagocytosis or liquid transport (pinocytosis) of the peptide into the cell.

Surprisingly, the presence of the adjuvant not only increases the uptake of the peptide into the cell but also results in a potentiation of the immunomodulatory effect of the peptide, which would appear to be due to correct presentation of the peptide by MHC-molecules.

In one embodiment, adjuvants, inter alia, may theoretically all be the membrane-permeabilising substances which are used for transporting nucleic acids into the cell; in connection with this, reference is made to WO 93/19768, which mentions such substances.

In a preferred embodiment of the invention, the adjuvant is a basic polyamino acid or a mixture of basic polyamino acids.

The degree of polymerisation of the polyamino acids may vary over a wide range. It may be about 5 to about 1000, more particularly about 15 to 500.

Preferably, polyarginine is used as the adjuvant within the scope of the present invention.

Another preferred adjuvant for the purposes of this invention is polylysine.

Examples of other suitable, particularly polycationic, organic compounds (basic polyamino acids) are polyornithine, histones, protamines, polyethyleneimines or mixtures thereof.

The adjuvant is optionally conjugated with a cellular ligand (e.g. with transferrin, gp120, LDL (Low Density Lipoprotein), α-fetuin, EGF (Epidermal Growth Factor) peptides or with a representative of other cellular ligands which have been described for the transportation of DNA by means of receptor-mediated endocytosis in WO 93/07283, carbohydrate residues such as mannose or fucose (ligands for macrophages) or antibodies or antibody fragments against cell surface proteins.

Optionally, polycationic adjuvants such as polyarginine or polylysine, which are optionally conjugated with a cellular ligand, occur as the constituents of a complex with DNA, e.g. in the form of plasmid DNA. The DNA may be free from sequences coding for functional peptides, in which case the DNA is an empty plasmid.

In one embodiment of the invention, the DNA contains sequences which code for immunomodulatory proteins, especially cytokines such as IL-2, interferons and GM-CSF.

In order to investigate the mechanism of the peptide transportation mediated by basic polyamino acids, the release of lactate dehydrogenase (LDH) was measured within the scope of the present invention. Whereas in polyarginine-treated samples the concentrations of released LDH were virtually undetectable, after incubation with polylysine high LDH concentrations were detected in the cell supernatants. These results lead one to conclude that the effect of polylysine must be due to permeabilisation of the cell membrane.

Without wishing to be tied to the theory, the effect of the pharmaceutical composition according to the invention would appear to consist in the fact that the peptide penetrates into the target cells with the help of the adjuvant or binds to cells which occur in the endodermal region of the skin. Target cells include, for example, antigen-presenting cells by which the peptide, optionally after processing, is presented to the B- and/or T-cells. Examples of target cells are macrophages, fibroblasts, keratinocytes, Langerhans cells, dendritic cells or B-cells.

Within the scope of the present invention, investigations were carried out to find out whether small peptides are absorbed to a greater degree by macrophage-like antigen-presenting cells (APCs) in the presence of basic polyamino acids or glycosylated forms of polycation. Regarding the sugar residues used, it is known that they are absorbed by macrophages using receptor mediated endocytosis. (As for APCs, it is assumed that in vivo they constitute the type of cell which absorbs the peptides and presents other immune cells. Results of in vitro tests which show that APCs endocytose increased quantities of peptide antigens in the presence of the adjuvants tested are an indication that these adjuvants are also suitable, in vivo, for potentiating the presentation of the peptides to the cytotoxic effector cells and the activation thereof, leading to an overall more powerful immune response to the target contained in the vaccine.)

The adjuvants used may also be components in particle form, optionally in addition to the adjuvants mentioned above. The particles may theoretically be any materials which are also used to produce column material for peptide synthesis, e.g. silica gel or synthetic resins, provided that they are physiologically acceptable and particles can be produced from them which are small enough to enter the cells. Using adjuvants in particle form it is possible to achieve high local concentrations of peptide, making it easier for it to be absorbed into the cells.

The type of adjuvant used, the suitability of modification thereof with a cellular ligand or the addition of DNA and the necessary quantity of adjuvant in relation to peptide may be determined empirically, e.g. the particular ratio of peptide to adjuvant chosen, which may theoretically vary over a wide range, can be determined by titration.

Adjuvants may in theory be tested by the same methods as the peptides, optionally in a number of steps:

The ability of an adjuvant to increase the binding and/or internalisation of a peptide to APCs may be measured, for example, in a first step by incubating APCs with fluorescent-labelled peptides and adjuvant. An increased uptake or binding brought about by the adjuvant can be determined by throughflow cytometry by comparison with cells mixed with peptide on its own.

In a second step the adjuvants to be tested can be investigated in vitro to see whether and to what extent their presence results in presentation of a peptide to APCs, and the method used for testing peptides above may be used to measure the MHC-concentration on the cells.

Another possible way of testing the efficiency of an adjuvant is to use an in vitro model system. Here, APCs are incubated together with adjuvant and peptide and the relative activation of a T-cell clone which specifically recognises the peptide used is measured (Coligan et al., 1991; Lopez et al., 1993).

The efficiency of the formulation may also be demonstrated by means of the cellular immune response by demonstrating a delayed-type hypersensitivity (DTH) reaction in immunised animals.

Finally, the immunomodulatory effect of the formulation is measured in animal trials. Established tumour models may be used, with peptide sequences recognised by immune cells. The vaccine containing peptide and adjuvant is administered in varying proportions with regard to the amount of peptide to adjuvant and the total amount. The protection from tumour growth is a measurement of the effectiveness of a tumour vaccine.

The pharmaceutical composition may be administered parenterally, topically, orally or locally. It is preferably given by parenteral, e.g. subcutaneous, intradermal or intramuscular route, preferably by subcutaneous or intradermal route, in order to reach skin cells in particular (keratinocytes, fibroblasts), dendritic cells, Langerhans cells or macrophages as the target cells. Within the scope of tumour therapy the tumour vaccine may also be administered by intratumoral route.

The composition according to the invention for parenteral administration is generally in the form of a solution or suspension of the peptide and adjuvant in a pharmaceutically acceptable carrier, preferably an aqueous carrier. Examples of aqueous carriers which may be used include water, buffered water, saline solution (0.4%), glycine solution (0.3%), hyaluronic acid and similar known carriers. Apart from aqueous carriers it is also possible to use solvents such as dimethylsulphoxide, propyleneglycol, dimethylformamide and mixtures thereof. The composition may also contain pharmaceutically acceptable excipients such as buffer substances and inorganic salts in order to achieve normal osmotic pressure and/or effective lyophilisation. Examples of such additives are sodium and potassium salts, e.g. chlorides and phosphates, sucrose, glucose, protein hydrolysates, dextran, polyvinylpyrrolidone or polyethyleneglycol. The compositions may be sterilised by conventional methods, e.g. by sterile filtration. The composition may be decanted directly in this form or lyophilised and mixed with a sterile solution before use.

In one embodiment, the pharmaceutical composition according to the invention is in the form of a topical formulation, e.g. for dermal or transdermal application. The pharmaceutical composition may, for example, take the form of hydrogel based on polyacrylic acid or polyacrylamide (such as Dolobene®, Merckle), as an ointment, e.g. with polyethyleneglycol (PEG) as the carrier, like the standard ointment DAB 8 (50% PEG 300, 50% PEG 1500), or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin, as well as pyrrolidones, e.g. 2-pyrrolidone, N-methyl-2-pyrrolidone, 2-pyrrolidone-5-carboxylic acid or the biodegradable N-(2-hydroxyethyl)-2-pyrrolidone and the fatty acid esters thereof, urea derivatives such as dodecylurea, 1,3-didodecylurea and 1,3-diphenylurea, terpenes, e.g. D-limonene, menthone, a-terpinol, carvol, limonene oxide or 1,8-cineol.

Other formulations are aerosols, e.g. for administering as a nasal spray or for inhalation.

The composition according to the invention may also be administered by means of liposomes which may take the form of emulsions, foams, micelles, insoluble monolayers, phospholipid dispersions, lamella layers and the like. These act as carriers for conveying the peptides to their target of a certain tissue, e.g. lymphoid tissue or tumour tissue or to increase the half-life of the peptides.

If the composition according to the invention is in the form of a topical formulation it may also contain UV-absorbers in order to act, for example, as a sun protection cream, for example, when the formulation is used prophylactically against melanoma.

The person skilled in the art will find suitable formulations and adjuvants in standard works such as "Remington's Pharmaceutical Sciences", 1990.

SUMMARY OF FIGURES

FIG. 1: Vaccination of DBA/2 mice against mastocytoma P815 with peptide KYQAVTTTL (SEQ ID NO:3)

FIG. 3: Vaccination of DBA/2 mice against mastocytoma P815 with peptide SYFPEITHI (SEQ ID NO:4)

FIG. 5: Vaccination of DBA/2 mice against melanoma M-3 by topical application FIG. 6: Vaccination of DBA/2 mice against melanoma M-3 metastases

FIG. 11: Potentiating the binding of peptides to APCs by basic polyamino acids

FIG. 12: Permeabilising the cell membrane by basic polyamino acids (LDH release after treatment of cells with polylysine or polyarginine)

FIG. 14: Transporting of peptides into antigen-presenting bone marrow cells

FIG. 16: Transport efficiency as a function of the degree of polymerisation of basic amino acids

A) Cells a) Cell lines

Figure 2B:
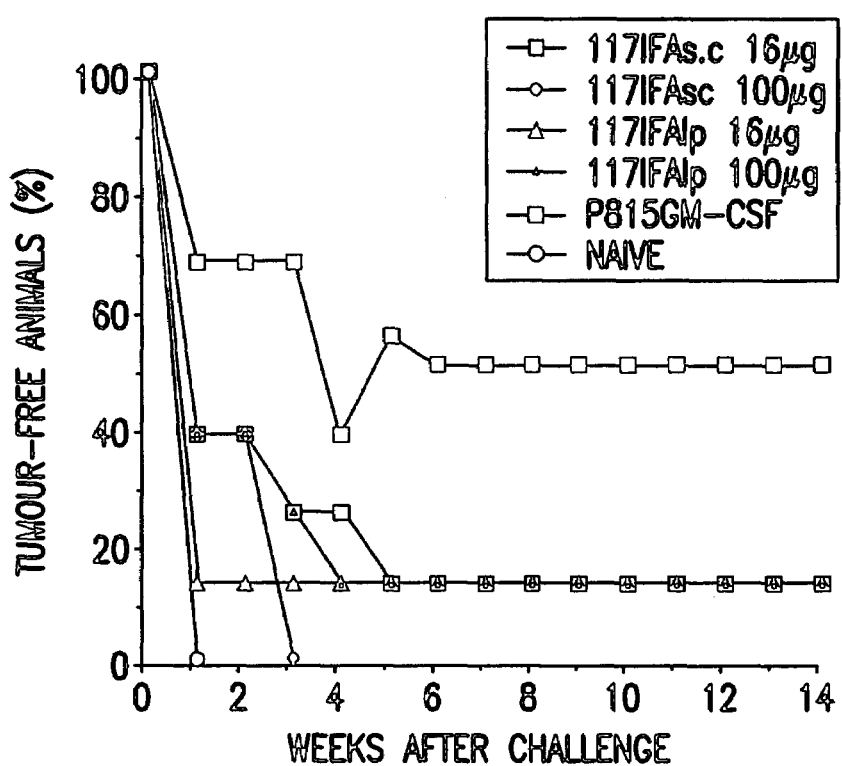
FIG. 2: Vaccination of DBA/2 mice against mastocytoma P815 with peptide SYFPEITHI (SEQ ID NO:4)

The murine melanoma cell line Cloudman S91 (clone M-3; ATCC No. CCL 53.1), the mastocytoma cell line P815 (ATCC No. TIB 64) and the monocyte macrophage cell line P388D1 (ATCC TIB 63) were obtained from ATCC. The cells were cultivated in DMEM medium with a high glucose content (High Glucose DMEM, Life Technologies) supplemented with 10% FCS, 2 mM L-glutamine and 20 µg/ml of gentamycin. The cells were routinely tested for the absence of *mycoplasma* contamination (PCR-*Mycoplasma* Detection Kit, Stratagene).

The murine cell line RMA/S (murine lymphoma) was described by Kärre et al, 1986 and by Ljunggren et al., 1990.

b) Antigen-presenting cells from bone marrow

First, the femurs from DBA/2 mice were rinsed. The bone marrow cells were cultivated in high glucose DMEM medium containing 10% FCS, 5% equine serum, 2 mM L-glutamine and 20 μg/ml gentamycin in the presence of 200 units/ml of murine GM-CSF (Li et al., 1989; Genzyme, Cambridge, Mass., USA). For the first five days two-thirds of the medium were changed every 24 hours to remove non-adhering granulocytes and B-cells (Inaba et al., 1992). Both adhering and loosely adhering cells were harvested between days 8 and 10 by incubation with PBS/5 mM EDTA and seeded out, at a cell density of $3\times10^4$ cells per well, on 8-well microscope slides (Nunc, Roskilde, Denmark). More than 90 of the cells showed a positive reaction with the antibody F4/80 (Endogen, Cambridge, Mass., USA).

B) Peptide synthesis

The peptides were synthesised in a peptide synthesiser (Model 433 A with feedback monitor, Applied Biosystems, Foster City, Canada) using TentaGel S PHB (Rapp, Tübingen) as a solid phase using the Fmoc method (HBTU activation, Fastmoc™, scale 0:25 mmol). The peptides were dissolved in 1 M TEAA, pH 7.3, and purified by reverse chromatography on a Vydac C 18 column. The sequences were confirmed by flight time mass spectrometry on an MAT Lasermat (Finnigan, San Jose, Canada).

C) List of the peptides used

| Name of peptide | Sequence | Associated antigen | Amino acid numbering in protein | MHC-haplotype |
|---|---|---|---|---|
| kpep117 | SYFPEITHI | Tyrosine-kinase JAK1 | 355–363 | $H2\text{-}K^d$ |
| kpep118 | KYQAVTTTL | Tum-P198 | 14–22 | $H2\text{-}K^d$ |
| Kpep162 | GPPHSNNFGY | Tum-P35B | 4–13 | $H2\text{-}D^d$ |
| Kpep163 | ISTQNHRAL | P91A | 12–20 | $H2\text{-}L^d$ |
| Kpep164 | LPYLGWLVF | P815 | 35–43 | $H2\text{-}L^d$ |
| kpep143 | RYAEDYEEL | trp-1 | | $H2\text{-}K^d$ |
| kpep145 | PYLEQASRI | tyrosinase | | $H2\text{-}K^d$ |
| kpep146 | YYVSRDTLL | tyrosinase | | $H2\text{-}K^d$ |
| kpep150 | YYSVKKTFL ASNENMETM | trp-1 influenza nucleocapsid peptide | | $H2\text{-}K^d$ |

Peptide mixtures:

Peptide mixture I for M-3 melanoma vaccine: kpep143, kpep145, kpep146, kpep150.

Peptide mixture III for mastocytoma P815 vaccine: kpep117, kpep188, Kpep162, Kpep163, Kpep164

D) Preparation of the vaccines

D1) Individual peptide vaccines a) Individual peptide control vaccines without adjuvant were prepared by taking up the peptide in a concentration of 1 mg/ml in PBS. The incubation period up to injection was 4 hours at ambient temperature.

b) Individual peptide vaccines with polylysine as adjuvant (unless otherwise stated polylysine with a chain length of 200 was used) were prepared by mixing peptide and polylysine in the specified amounts in HBS. The incubation time up to injection was 4 hours at ambient temperature.

i) In order to obtain a vaccine containing 16 μg of effective peptide, 11.8 μg of polylysine were mixed with 160 μg of peptide kpep117 in a total volume of 1 ml of HBS.

ii) In order to obtain a vaccine containing 100 μg of effective peptide, 74 μg of polylysine were mixed with 1 mg of peptide kpep117 in a total volume of 1 ml HBS.

c) Individual peptide control vaccines with incomplete Freund's adjuvant (IFA) were prepared by emulsifying peptide and IFA in the amounts specified. The incubation time up to injection was 30 minutes at ambient temperature.

i) For a control vaccine containing 16 μg of active peptide, 192 μg of peptide kpep117 were emulsified in 600 μl of HBS with 600 μl of IFA.

ii) For a control vaccine containing 100 μg of effective peptide, 1.2 mg of peptide kpep117 were emulsified in 600 μl of HBS with 600 μl of IFA.

D2) Peptide mixtures as vaccines a) Peptide mixture I as a control vaccine without adjuvant contained 250 μg of each of the peptides kpep143, kpep145, kpep146 and kpep150 in a total volume of 1 ml PBS.

b) Peptide mixture III as a control vaccine without adjuvant contained 250 μg of each of the peptides kpep117, kpep118, Kpep162, Kpep163 and Kpep164 in a total volume of 1 ml of PBS.

c) Peptide mixture I as a vaccine with polylysine as adjuvant was prepared by mixing 1 mg of peptide mixture I (containing 250 μg of each peptide) with 74 μg of polylysine in HBS. The incubation period up to injection was 4 hours at ambient temperature.

d) Peptide mixture III as a vaccine with polylysine as adjuvant was prepared by mixing 1.25 mg of peptide mixture III (containing 250 μg of each peptide) with 93 g. of polylysine in HBS. The incubation period up to injection was 4 hours at ambient temperature.

e) Peptide mixture I as a control vaccine with incomplete Freund's adjuvant was prepared by emulsifying 1.2 mg of peptide mixture I in 600 μl of HBS (containing 300 μg of each peptide) with 600 μl of IFA. The incubation time up to injection was 30 minutes at ambient temperature.

f) Peptide mixture III as control vaccine with incomplete Freund's adjuvant was prepared by emulsifying 1.5 mg of peptide mixture III in 600 μl of HBS (containing 300 μg of each peptide) with 600 μl of IFA. The incubation time up to injection was 30 minutes at ambient temperature.

g) For topical application with polylysine as adjuvant, 1 mg of peptide mixture I (containing 250 μg of each peptide) was incubated with 74 μg of polylysine for 4 hours in a total volume of 400 μl of HBS. The mixture obtained was stirred into 1.6 g of the hydrogel DOLOBENE (Merckle).

h) For topical administration of a control vaccine without an adjuvant, 1 mg of peptide mixture I (containing 250 μg of each peptide) in a total volume of 200 μl of HBS was stirred into 1.8 g of the hydrogel DOLOBENE (Merckle).

i) The preparation of fucose-coupled polylysine (chain length: 240) was carried out using the method described by MacBroom et al., 1992, achieving a substitution of about 40% (the starting materials β-L-fucopyranosylphenyl-isothiocyanate and polylysine were obtained from Sigma).

j) When transferrin/polylysine-conjugates (prepared as described in WO 93/07283) were used, the quantity was adjusted so that the absolute quantity of polylysine was 75

μg per mg of peptide. When plasmid. DNA (empty plasmid pSP65, LPS-free, Boehringer Mannheim) was integrated in the complexes, the ratio was 37.5 μg of DNA/75 μg of polylysine/1 mg of peptide. When 160 μg were used instead of 1 mg of peptide, the quantities of the other components were reduced by the same factor (6.25).

E) Injection of the vaccines

Before the subcutaneous injection the mice were anaesthetised in an isolated air chamber in groups of up to eight animals. After 3.5 minutes of halothane treatment (4% in $O_2$, flow rate 4) the mice were anaesthetised for about 1 minute; during this time the vaccines were injected subcutaneously.

The intraperitoneal injection was given without any previous anaesthetic. The volume of the injection was 100 μl of each vaccine per animal, corresponding to 100 μg of individual peptide or peptide mixture I per animal. In the case of peptide mixture III, the total amount of peptide administered to each mouse was 125 μg.

F) Topical application of the vaccines

For each mouse, 200 mg of ointment containing 100 μg of peptide or peptide mixture 1 or 125 μg of peptide mixture I was rubbed into the skin of the shaved animals, all over their back and in their ears. The correct quantity was monitored using scales.

G) Use of the vaccine against tumour growth in the mouse model

The procedure for testing the efficacy of the cancer vaccines in the prophylactic or therapeutic mouse model corresponded to the principle described in WO 94/21808, unless otherwise specified, using the DBA/2 model as the mouse model.

Example 1

Vaccination of DBA/2 mice against mastocytomas P815

160 μg of the peptide of sequence KYQAVTTTL (SEQ ID NO:3) (kpep118) derived from the tumour antigen P815 described by Lethe et al., 1992, a ligand of H2-$K^d$, was mixed with 11.8 μg of polylysine 300 in 500 μl of HBS and incubated for 4 hours at ambient temperature. Then 500 μl of EBSS (Earl's buffered saline) were added. 100 μl portions of the resulting mixture were administered subcutaneously to 8 mice at intervals of one week. After this pre-immunisation, tumours were set after another week, by injecting each mouse contralaterally with $5 \times 10^4$ cells of the mastocytoma cell line P815 (ATCC No. TIB 64; these cells express the tumour antigen from which the peptide P815 is derived) in 100 μl of EBSS. The results of these tests are shown in FIG. 1 (filled-in squares).

In a parallel trial, 200 μg of the peptide were mixed with 500 μl of HBS and then emulsified with 500 μl of Freund's adjuvant. 8 mice were pre-immunised with 100 μl of the resulting emulsion and then tumours were set with P815 cells as described above (FIG. 1: filled-in circles).

For another parallel experiment, a cellular tumour vaccine was prepared as follows:

160 μg of peptide kpep 118 were mixed with 3 μg of transferrin-polylysine (TfpL), 10 μg of pL and 6 μg of plasmid psp65 (LPS free) in 500 μl of HBS buffer. After 30 minutes at ambient temperature the above solution was added to a T 75 cell culture flask with $1.5 \times 10^6$ cells of the allogenic fibroblast cell line NIH3T3 (ATCC No. CRL 1658) in 20 ml of DMEM medium (10% FCS, 20 mM glucose) and incubated at 37° C. After 3 hours, the cells were mixed with 15 ml of fresh medium and incubated overnight at 37° C. with 5% $CO_2$. 4 hours before administration, the cells were irradiated with 20 Gy. The vaccine was prepared as described in WO 94/21808. The pre-immunisation with this vaccine was carried out at intervals of one week with $10^5$ cells; after another week; the tumors were set as described above (FIG. 1: filled-in triangles). It was found that the vaccine containing the peptide combined with polylysine offered best protection for the mice against tumour formation.

Example 2

Vaccination of DBA/2 mice against mastocytoma P815 with a single peptide vaccine a) Three single peptide vaccines containing either peptide kpep117 on its own in PBS (FIG. 2a), peptide kpep117 emulsified in IFA (FIG. 2b) or peptide kpep117 with polylysine (chain length: 240) as adjuvant (FIG. 2c) were tested for their protective effect against a P815 tumour challenge. The vaccines were prepared as described in Section D above. The injection volume was 100 μl in each case; the injection was given subcutaneously (sc) or intraperitoneally (ip). Naive mice were used as a negative control, a whole cell vaccine consisting of GM-CSF secreting P815 cells was the positive control (P815-GM-CSF; $10^5$ cells in 100 μl were injected subcutaneously into each animal). Each experimental group consisted of eight animals and three vaccinations (sc) were carried out at seven day intervals. One week after the last vaccination the animals were given a contralateral tumour challenge with $5 \times 10^4$ P815 cells. The animals were inspected daily and the appearance of any tumours was monitored at weekly intervals.

Figure 2C:
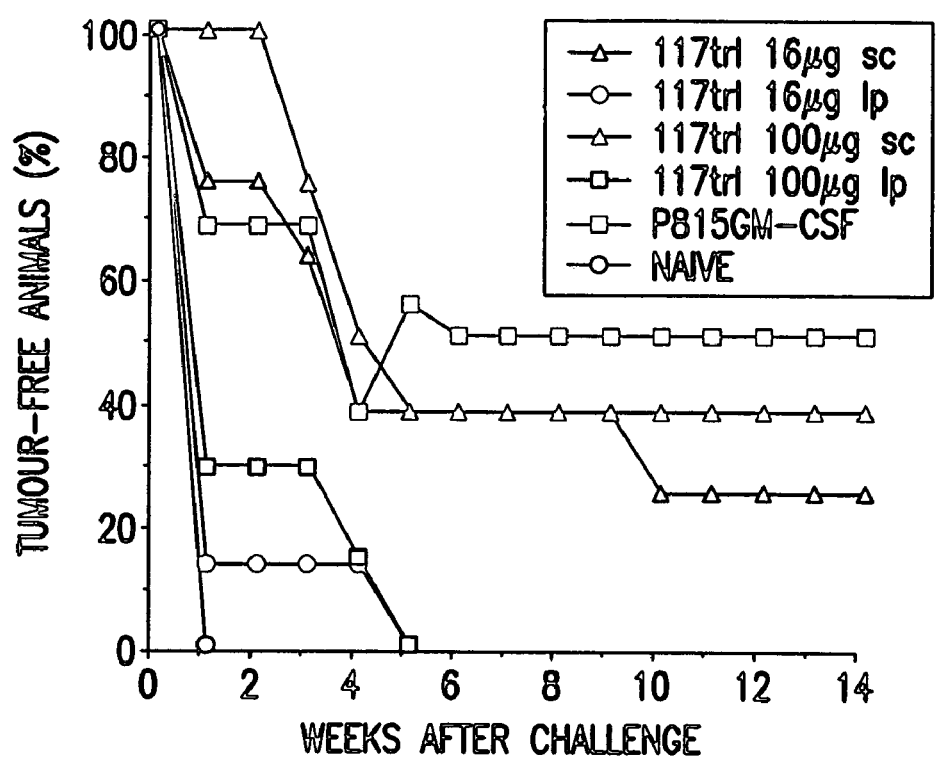

Peptide kpep117 with polylysine as adjuvant produced the best antitumour effect when 100 μg were injected subcutaneously into each animal (three of the eight animals were protected). This effect was approximately as good as the one achieved with the whole cell vaccine (four out of eight animals protected). 16 μg of peptide together with polylysine per animal was less effective (two animals protected), but significantly better than 100 μg of peptide in PBS (FIG. 2a, no protective effect). Also when emulsified in IFA the peptide did not achieve the activity which it achieved together with polylysine (FIG. 2c).

b) In another experiment on the P815 mastocytoma model, two unmodified polylysines of different chain lengths were compared with each other, a short one with only 16 lysine groups (pL16) and a long one with 240 groups (pL240). The animals in the control groups were injected with 100 μg of peptide kpep 117, either dissolved in PBS or emulsified in IFA. Two GM-CSF-secreting cellular control vaccines were used as positive controls (cf. a)), one vaccine being obtained from stably transfected P815 cells and the second vaccine being obtained by transient transfection using the method described by Wagner et al., 1992 (AVET). The two whole cell vaccines confer protection on four or five of the total of eight animals. Peptide-based vaccines consisting of peptide on its own or the peptide emulsified in IFA showed no protective effect; all the animals developed tumours rapidly after the tumour challenge. However, if the peptide was administered together with polylysine, the peptide vaccines protected the animals from the tumour challenge: two out of the eight animals were protected when the long polylysine (pL240) was used, and four out of the eight animals in the case of the short polylysine. These results, which are shown in FIG. 3, demonstrate that a single peptide, when administered with polylysine as adjuvant, provides efficient antitumour protection which is comparable with that of one of the most effective cytokine-secreting whole-cell vaccines mentioned in the literature as the standard for antitumour vaccination (Dranoff et al., 1993; Schmidt et al., 1995).

Example 3

Vaccination of DBA/2 mice against mastocytoma P815 with a tumour vaccine containing P815 single peptide or mixtures of P815 peptides The following peptides were used to prepare the vaccine:
kpep118 (100 µg per injection)
Peptide mixture III (kpep117, kpep118, kpep162, kpep163, kpep164): this peptide mixture contains all the P815 peptides known hitherto; 25 µg of each peptide were administered in each injection).

GM-CSF secreting P815 cells were used as the positive control.

In preliminary tests, kpep117 proved to be the peptide with the best protective effect against P815 tumour setting when 100 µg of peptide were used together with polylysine (7.5 µg of polylysine/100 µg of peptide, corresponding to the standard ratio; polylysine: chain length=200). A smaller amount (16 µg) of kpep117 had been less effective. In this example, 100 µg of kpep118 were injected into each animal, on one occasion with only polylysine (group B), then with transferrin-polylysine (group C) and again with transferrin-polylysine/DNA (group D). kpep118 with IFA was used as control. In this experiment, kpep118 on its own showed no protective effect against tumour setting.

In the experiments carried out in Example 4, it was shown that a vaccine containing a peptide mixture of melanoma peptides had a protective effect against melanoma. Therefore, this example was used to test whether the concept of the peptide mixture is also suitable for P815.

The peptide mixture III was administered once with only polylysine (group E), once with transferrin-polylysine (group F) and once with transferrin-polylysine/DNA (group G). Peptide mixture III in IFA was used as the control. Naive mice were used as the negative control; GM-CSF-transfected P815 cells were used as the positive control ($10^5$ cells per mouse).

The experiments carried out in this Example proved to be rather untypical, compared with the other experiments: in the positive control group (GM-CSF secreting cells) all the animals developed tumours shortly after tumour setting, and the majority of these tumours disappeared just as quickly as they had formed. One possible explanation for this is that the tumour grew for a while before it was destroyed. A second possible explanation would be that the swelling diagnosed as a tumour did not originate from tumour growth but was the result of a powerful immune cell infiltration (granuloma). Since the animals were not dissected the reason could not be established definitively; in any case, the tumours produced were finally destroyed. Another interesting result was obtained in group G in which the animals were treated with a combination of peptide mixture III and polylysine. All the animals developed tumours, but in two of the animals the size of the swelling of the tumour (or the immune cell infiltration) was relatively small, did not increase, and the mice did not look unhealthy. These two animals were not killed but were kept under observation. Surprisingly, the tumours were undetectable nine weeks after tumour setting, a result which had not been observed before. Finally, two out of eight animals destroyed their tumours. The destruction of the tumours would appear to be a result of the content of kpep117 in the peptide mixture, which would be analogous to Example 2, in which two out of eight animals were protected with 16 µg of kpep117 and three out of eight animals were protected with 100 µg of kpep117. However, the protective effect might also have been produced by more than one peptide in the mixture.

Example 4

Protection of DBA/2 mice against melanoma M-3 by pre-immunisation with a tumour vaccine containing a mixture of peptides A prophylactic vaccine was used containing a mixture of melanoma peptides (peptide mixture I, paragraph D2).

Figure 4:
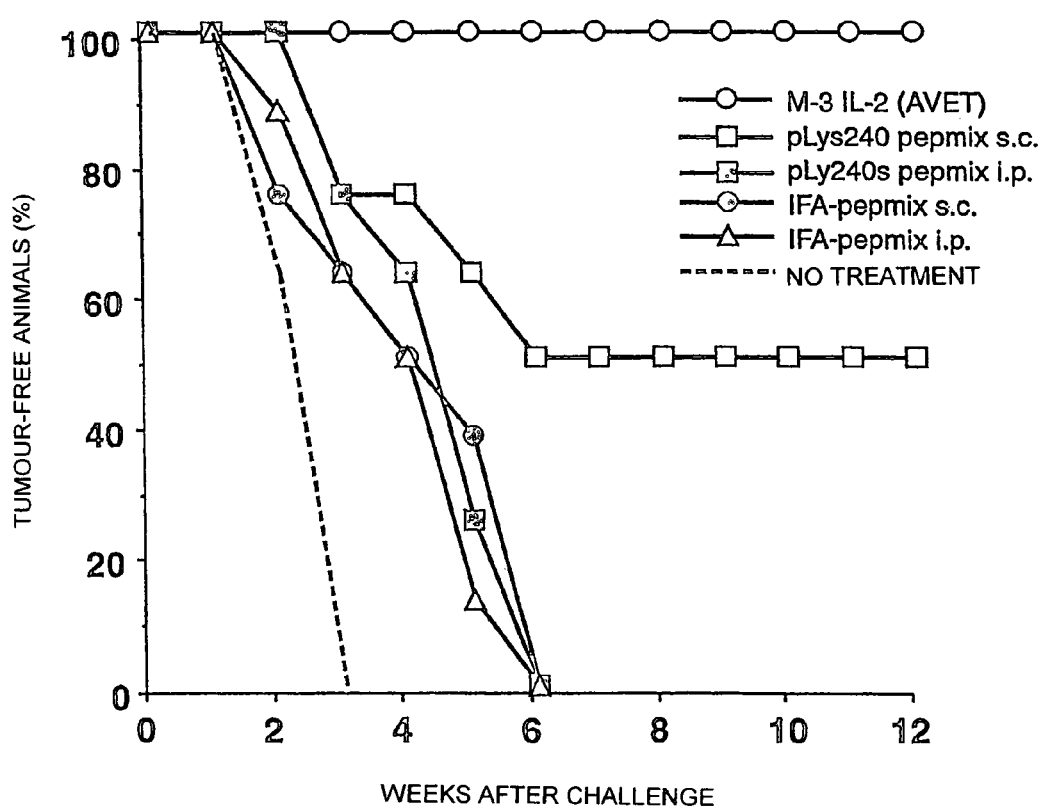
FIG. 4: Vaccination of DBA/2 mice against melanoma M-3 with a mixture of peptides

The procedure for pre-immunisation with the vaccine and the setting of the tumours corresponded to the procedure described in Example 2, except that the tumour setting was carried out with M3 cells ($10^5$ cells per animal). The control vaccine used was a whole cell vaccine from M-3 cells which secrete an optimum amount of IL-2 (1000–2000 units per $10^5$ cells) and prepared as described by Schmidt et al. 1995. Under the test conditions used, this vaccine achieved 100% protection (FIG. 4). Four groups of experimental animals were given the vaccines with the peptide mixture. Two groups were given the peptides emulsified in IFA, either s.c. or i.p. The other two groups were given the peptides together with polylysine (pL240), either s.c. or i.p.

FIG. 4 illustrates the protective effect of the peptide vaccines with polylysine (pL240) as adjuvant; 50% of the treated mice were protected from the M-3 tumour challenge, compared with the untreated animals, in which solid tumours rapidly developed. This effect could be achieved if the peptide-polylysine vaccine was injected subcutaneously or applied to the skin as a hydrogel (FIG. 5). In the other three control groups, which were treated with the peptide/polylysine vaccines i.p. or with peptides in IFA, the vaccine was essentially ineffective. Here, the tumours set were not rejected, and the tumours grew with only a slight delay compared with the untreated control animals. These results show that a vaccine containing a peptide mixture achieves an antitumour protective effect if it contains polylsine. Under the test conditions chosen, this peptide vaccine was only half as effective as the cellular IL-2-vaccine which, in conformity with reports that have appeared recently (Zatloukal, 1993, Zatloukal, 1995), protected up to 100% of the animals against the tumour challenge with $10^5$ live M3 cells.

Example 5

Protection of DBA/2 mice against M-3 metastases
a) A therapeutic vaccine was used containing a mixture of melanoma peptides (peptide mixture 1 described in paragraph D2). Three vaccinations (sc) were given at intervals of one week. The first vaccination was given five days after the setting of the metastases and consequently vaccination was given against a five day metastasis. $1.2 \times 10^4$ M-3 cells were injected for the metastasis setting, using the procedure described in WO 94/21808 and by Schmidt et al., 1996.

Figure 7B:
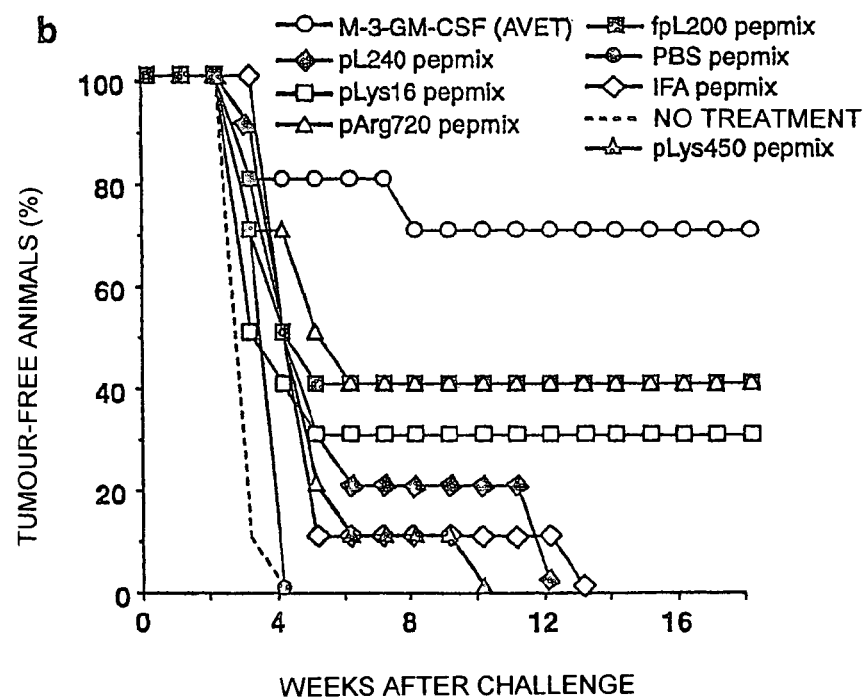
FIG. 7: Curing mice with M-3 micrometastases after vaccination with a peptide mixture

The vaccine used was peptide mixture I: without the adjuvant (pepmix1 PBS), with IFA as adjuvant (IFA pepmix1) or with fucose-modified polylysine (fpL pepmix1). The control groups were given no vaccine (naive) or the M-3 whole cell vaccine producing IL-2 mentioned in Example 4. FIG. 6 shows that the best protection was achieved in the group treated with peptide mixture 1 with fucose-modified polylysine as adjuvant (FIG. 6a). 50% of the mice were able to reject the metastases (⅘). This treatment was even more effective than the one with the whole cell vaccine which protected only 33% of the mice (⅗). The peptide vaccines with IFA or without adjuvant only resulted in a delay in the growth of the metastases into a tumour (FIG. 6b).

b) In another experiment, the protective effect of a vaccine which contained peptide mixture I and was administered subcutaneously was tested in a therapeutic model. Control groups were given the peptide mixture in PBS (without adjuvant) or with IFA. Unmodified polylysine 240 was used as adjuvant. In addition, fucose-modified polylysine 200 (fpL 200) was used as adjuvant. The control consisted of a group of animals with the IL-2 expressing cellular vaccine. As shown in FIG. 7a, the peptide/polylysine vaccine was effective in the treatment of M3-metastases. A significant cure rate was achieved in this experiment only with the fucose-modified polylysine. With this treatment, 50% of the animals rejected the metastases, which is a good result compared with the IL-2 vaccine, which cured 70% of the animals in this case.

c) In another experiment, the effect of changes and modifications to the polycation on the antitumour activity was tested on the therapeutic model. In addition to the unmodified and fucose-modified polylysine 200, the short unmodified polylysine pL16, a long polylysine pL450 and another polycation, namely polyarginine (pArg720) were tested. A cellular M3 vaccine secreting an optimum amount ($\geq 10$ ng per $10^5$ cells) of GM-CSF was used as the positive control (Schmidt, 1995). In this experiment, too, the control groups were given the peptide mixture in IFA or without any adjuvant. As in Example 5b), the best effect was achieved when fucose-polylysine was used as adjuvant (FIG. 7b). In these groups, 40% of the animals rejected the metastases, compared with 30% in the group with the short polylysine pL16. Apart from the group which had been given the peptides together with polyarginine, the animals in the other groups which had been given a peptide vaccine showed only a short delay before tumours formed. The unmodified polyarginine was just as effective in this test as the fucose-modified polylysine and led to the rejection of the metastases in four out of ten animals.

FIG. 7c shows a repetition of this effect achieved with polyarginine in an independent experiment. Here again, vaccination with the peptide mixture together with polyarginine exhibited an antitumour activity in four out of eight treated animals.

Example 6

Transloading of cells with tyrosinase using polylysine as adjuvant

This example was an experiment intended to show that polylysine is suitable as an adjuvant for loading cells with larger protein fragments or whole proteins, with M-3 cells being used as examples of cells.

Figure 8:
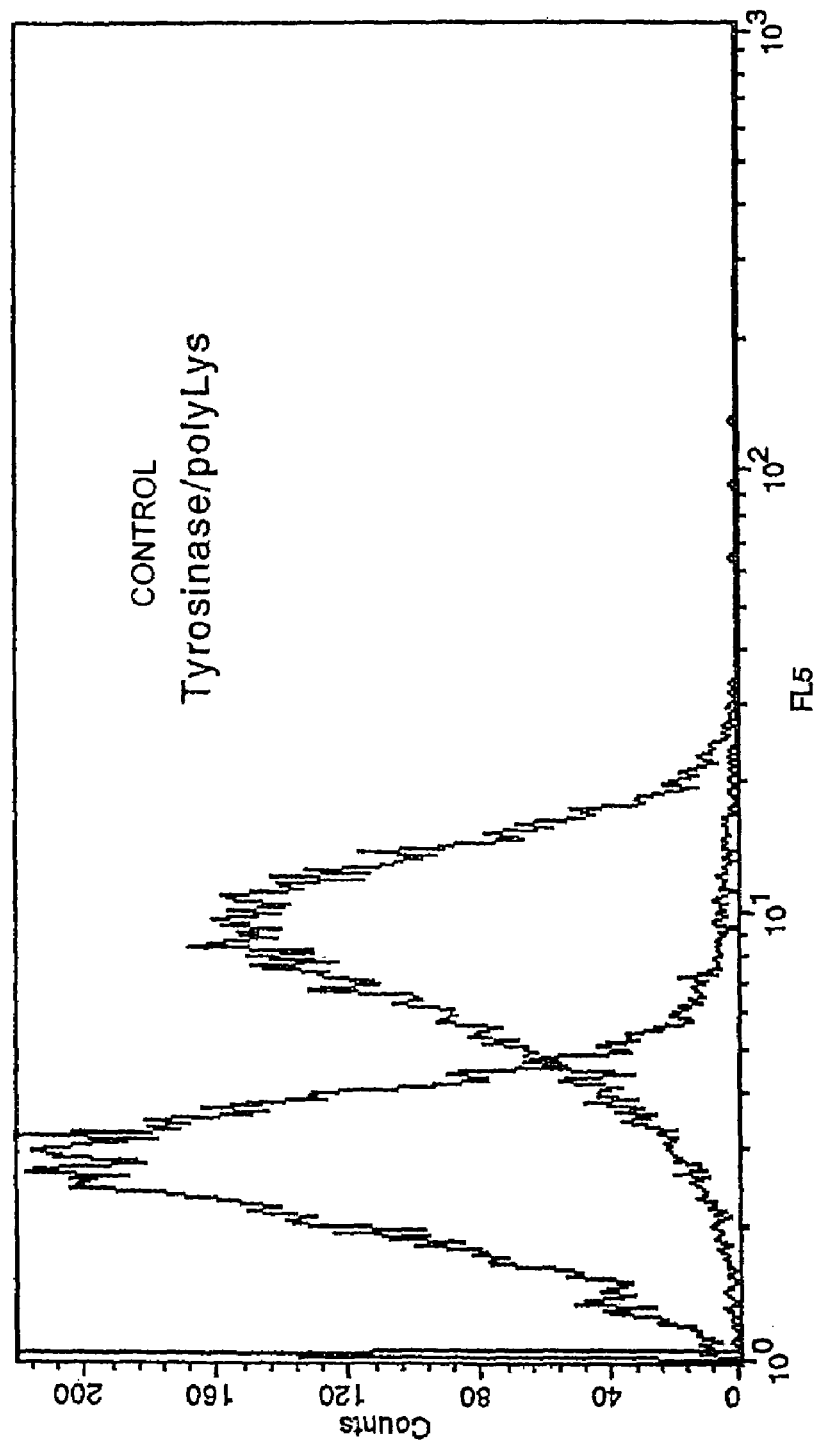
FIG. 8: Polylysine-mediated charging of cells with tyrosinase

For loading the cells, first of all 160 μg of FITC-labelled tyrosinase (EC 1.14.18.1; Sigma) were mixed with 3 μg of polylysine (pL240) and incubated for 3 hours at ambient temperature. Then the solution obtained was placed in a T 75 cell culture flask with $2 \times 10^6$ M-3 cells and incubated at 37° C. The cells were then washed twice with PBS, detached with PBS/2 mM EDTA and taken up in 1 ml PBS/5% FCS for FACS analysis. FIG. 8 shows the loading of M-3 cells with tyrosinase (the lefthand curve shows the control, the right-hand curve shows the loading with tyrosinase).

Example 7

Determining the T-cell activation after immunisation in the therapeutic model

After the peptide/polycation vaccine had clearly exhibited an effect in the therapeutic mouse model (cf. Example 5), an investigation was carried out to see whether this treatment also leads to the activation of T-cells. For this, cytokine secretion was used after co-incubation with spleen cells from vaccinated animals with parental M3 cells acting as markers (Kawakami et al., 1994b).

Figure 9:
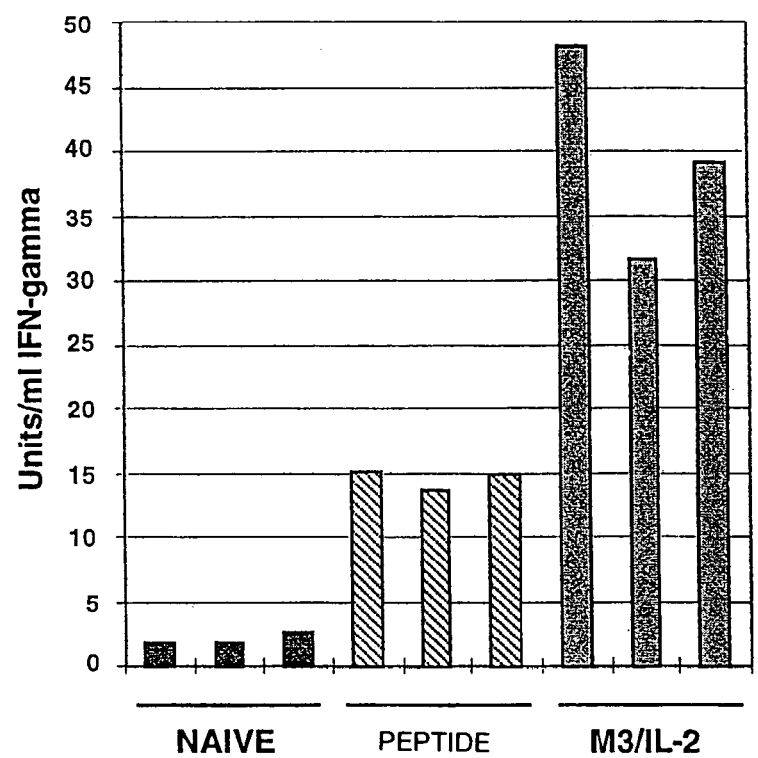
FIG. 9: T-cell activation after vaccination in the therapeutic model (IFN-γ release from spleen cells of vaccinated animals as a reaction to M-3 cells)

Single-cell spleen suspensions were prepared from vaccinated and untreated animals, followed by erythrocyte lysing with hypotonic buffer (0.15 NH$_4$Cl, 1 mM KHCO$_3$, 0.1 mM EDTA, pH 7.4). Adhering cells were removed by incubating $3 \times 10^6$ spleen cells per ml of DMEM medium (10% FCS) in Petri dishes for 90 minutes at 37° C. Non-adhering cells were co-cultivated by careful pipetting and co-cultivation with $1 \times 10^3$ of parental cells in various ratios. The cells were cultivated in 200 μl of DMEM medium (10% FCS), 2 mM L-glutamine and 20 μg/ml of gentamycin in 96 well flat-bottomed tissue culture dishes. On day 9, 100 μl of supernatant were harvested and the IFN-γ content was measured using a commercially available ELISA kit (Endogen, Cambridge, Mass., USA) according to the manufacturer's instructions. It was found that after nine days' incubation only spleen cells from vaccinated animals were secreting large amounts of IFN-γ into the medium, whilst in the co-cultures of spleen cells from untreated animals and M3 cells, virtually no IFN-γ could be detected. The results of these experiments are shown in FIG. 9.

Example 8

Induction of antiviral immunity by means of influenza nucleocapsid peptide ASNENMETM (SEQ ID NO:5) and fucosylated polylysine as adjuvant A vaccine was used which contained 75 g of fpLys per 1 mg of peptide ASNENMETM (SEQ ID NO:5). The vaccine was administered by a single injection, as stated in the method section, injecting 100 μg of peptide/7.5 μg of fpLys per animal. As a control, 100 μg of peptide was injected on its own (PBS) or no injection was given at all (naive control).

RMA-S mouse lymphoma cells were incubated overnight in serum-free medium at 26° C. with 10 g/ml of peptide ASNENMETM.

Figure 10:
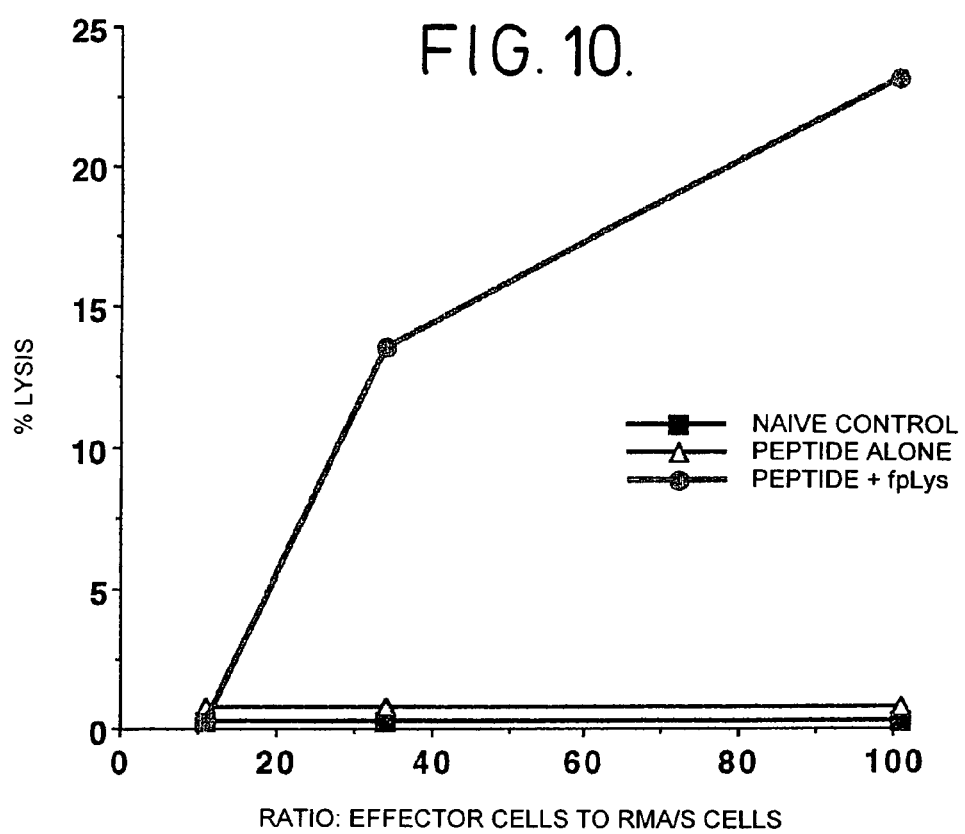
FIG. 10: Induction of antiviral immunity by means of influenza nucleocapsid peptide ASNENMETM (SEQ ID NO:5) and fucosylated polylysine as adjuvant (CTL activation)

10 days after the vaccination, spleen cells were isolated from the vaccinated animals, mixed with the peptide-laden RMA-S cells in the ratio 5:1 and cultivated for a further five days (Stuber et al., 1994). The number of surviving effector spleen cells in the various cultures was determined, then, in order to determine the CTL activity by means of the standard 4 h europium release assay (Blomberg et al., 1993), the cells were mixed in varying proportions with RMA-S cells which h been combined with the peptide ASNENMETM (SEQ ID NO:5) and with europium chelate. As shown in FIG. 10, the specific immunity was obtained in this test only by vaccination with peptide and fpLys, but not when the peptide was administered on its own.

Example 9

Testing of various basic polyamino acids for their ability to potentiate the internalising and/or binding of peptides to APCs For these tests a fluorescence assay was use: a model peptide antigen of the sequence LFEAIEGFI (SEQ ID NO:1) (MHC Kd-restricted) was labelled with the fluorescent dye fluorescein isothiocyanate (FITC) in accordance with the manufacturer's instructions (Molecular Probes). The uptake or binding of FITC-labelled peptide on its own ("pulsed") or together with various concentrations of basic amino acids (polylysine with a chain length of 16 to 490, polyarginine with a chain length of 15 to 720) by the MHC Kd-restricted monocyte macrophage cell line P388D1 was measured by throughflow cytometry. In order to do this, $1 \times 10^6$ P388D1 cells were incubated in a final volume of 1 ml of medium (DMEM/10% FCS) in a centrifugal test tube with 5 μg of FITC-labelled peptide on its own or with a mixture of peptide and polyamino acid for 30 minutes at 37° C. and then washed thoroughly to eliminate any free peptide. The polyamino acids were added in a concentration of 50, 25, 12, 6 and 3 μg per ml of medium, containing 5 μg of FITC-labelled peptide. The relative intensity of fluorescence of the various samples was compared in order to assess the efficiency of uptake and/or binding of the peptide. The results of these tests are shown in FIG. 11; the tests were carried out using 25 μg of pL450 and pArg450, respectively. Under the conditions used, polyarginine was found to be about five times more efficient than polylysine.

Example 10

Investigation of the mechanism by which peptides can be absorbed by APCs

Peptides can be absorbed by APCs by means of specific mechanisms such as macropinocytosis or receptor-mediated endocytosis (Lanzavecchia, 1996). An alternative mechanism may consist in the polyamino acids making the cell membrane permeable and in this way allowing peptides to diffuse from the medium into the cytoplasm.

a) The possible permeabilisation of the cell membrane was tested by measuring the release of the cytoplasmic enzyme lactate dehydrogenase (LDH) after the incubation of P388D1 cells with polyamino acids (polylysine or polyarginine) under isotonic conditions using the commercially available kit (Cytotox 96, Promega, Madison, Wis., USA) in accordance with the manufacturer's instructions. On the basis of the results in FIG. 12a it can be assumed that the effect of pLys consists in making the cell membranes permeable, which is expressed in high concentrations of cytoplasmic enzyme released under isotonic conditions. By contrast, after pArg treatment (FIG. 12b), virtually no LDH was detected. When samples treated with polyamino acids alone were compared, no difference in the release of LDH was found compared with treatment with a mixture of polylysine or polyarginine with peptide. After incubation with peptide on its own, no measurable LDH-activity was detected.

b) The possible internalisation of FITC-labelled peptides in the presence or absence of basic polyamino acids was investigated on the basis of the principle published by Midoux et al., 1993: particles internalised by cells are transported in endosomes. Compared with the cytoplasm or cell culture medium which have neutral pH values, these organelles with a pH of about 5 are acidic. The fluorescence emitted by FITC is strongly pH-dependent. In an environment with pH conditions such as those found in endosomes, fluorescence is suppressed. Therefore, FITC-labelled peptides which are absorbed by the cells into the endosomes show reduced fluorescence. When monensin is added, the low pH of the endosomes is neutralised, leading to a measurably greater fluorescence of the internalised FITC-labelled peptides.

The cells were incubated with a mixture of polyarginine (average molecular weight range 100,000, chain length 490) and fluorescence-labelled peptide at 4° C. or 37° C. One aliquot of the samples incubated at 37° C. was kept back and treated at 4° C. with 50 μM monensin before the analysis by throughflow cytometry.

It was found that the incubation of APCs with specific basic polyamino acids such as polylysine (pLys) and polyarginine (pArg) intensifies the uptake or binding of the peptides to APCs.

Figure 13:
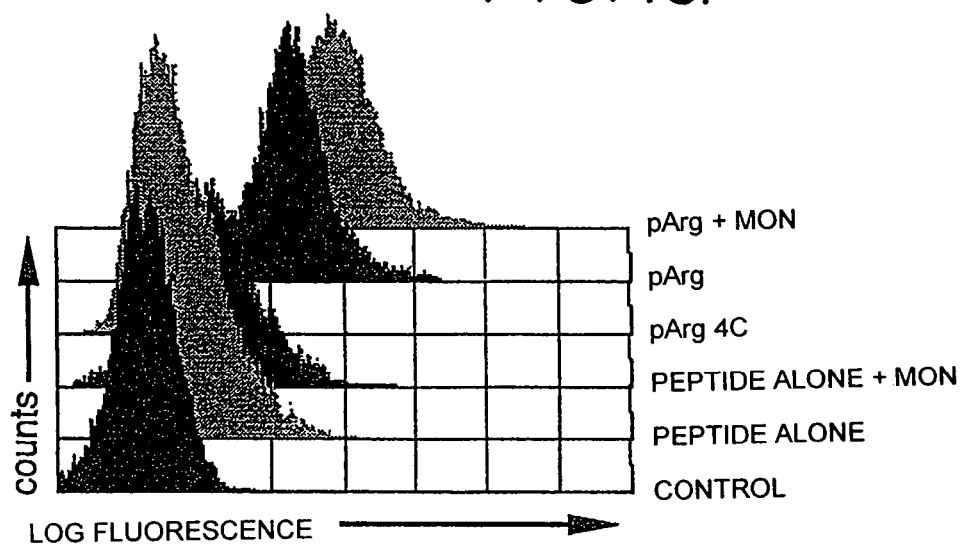
FIG. 13: Internalisation of peptides by polyarginine

As is apparent from FIG. 13, only a slight increase in fluorescence was observed in cells which had been treated with peptide alone and with monensin. By contrast, the fluorescence signals were greatly increased in samples which had been treated with monensin and a mixture of polyarginine and peptide. No uptake of peptide was observed when the samples were incubated at 4° C. A significant increase in fluorescence after treatment with monensin indicates that the loading of the peptides brought about with pArg causes them to accumulate in vesicles within the cell (Midoux et al., 1993; FIG. 13). As expected, after monensin treatment of polylysine-laden samples, only a slight increase in fluorescence was observed. Loading with polylysine at 4° C. brought about a measurable increase in fluorescence, which is a further indication that the effect of polylysine is chiefly caused by permeabilisation of the cell membranes (FIG. 12b).

Example 11

Investigating the loading of APCs with short peptides

APCs from bone marrow and obtained with GM-CSF were investigated by fluorescence microscopy with a combination of a fluorescence-labelled peptide plus polylysine (pL200; Sigma) or with peptide alone. For microscopic detection of the peptide uptake, the APCs were seeded out on slides and incubated with 40 μg of fluorescein-labelled peptide LFEAIEGFI (SEQ ID NO:1) on its own or with a mixture of 50 μg/ml of polylysine (pL200) and 40 μg/ml peptide LFEAIEGFI (SEQ ID NO:1) for 30 minutes at 37° C. After exhaustive washing, the cells were fixed with 4% para-formaldehyde, covered with anti-Fadent (Dako, Glostrup, Denmark) and subjected to fluorescence microscopy (Zeiss). The nuclei were counterstained with 4,6-diamidino-2-phenylindole (DAPI; Sigma). As shown in the fluorescence microphotographs in FIG. 14, the cells which had been incubated with peptide and polylysine (A) showed a significantly greater uptake of the peptide than the cells which had been treated with the peptide alone (B). Whereas the fluorescence occurred only sporadically and in particle form in the cells which had been treated ("pulsed") with peptide alone, the intensive fluorescence of the cells loaded with peptide in the presence of polylysine was non-localised and generally more uniformly distributed over the cell as a whole.

Example 12

Quantitative measurement of the loading of cells with peptide using throughflow cytometry (transloading assay)

a) After the tests carried out in Example 11 had showed that APCs are excellent target cells for loading with small peptides, FACS assays were carried out in vitro in order to identify suitable adjuvants for peptide vaccines. This assay permits rapid quantitative testing of fluorescence-labelled peptides; the peptide of sequence LFEAIEGFI (SEQ ID NO:1) was used as the model peptide. In these tests, the murine cell line P388D1 was used as the APCs. $10^6$ cells were incubated in a final volume of 1 ml of high glucose DMEM medium and 10% FCS for 30 minutes at 37° C. with 5 µg of peptide at a final fluorescein concentration of 5 nmol/ml. The cells were treated either with peptide alone or with a combination of peptide and polycations or peptide and histones at increasing concentrations (3 to 50 µg/ml), as stated in FIG. 15. The following compounds are used: A: polyornithine (average molecular weight range 110,000, chain length 580); B: arginine-rich histone; C: lysine-rich histone; D: polyarginine (average molecular weight range 100,000, chain length 490); E: polylysine (average molecular weight range 94,000, chain length 450). In preliminary tests it was found that an incubation period of 0.30 minutes yielded the maximum peptide uptake. Longer treatment (4 or 8 hours) did not produce any significant increase in the fluorescence signal. Before the analysis the cells were washed 5 times with a large volume of PBS containing 0.2% BSA. The cells were taken up in 1 ml of ice-cold PBS/0.2% BSA and investigated by throughflow cytometry (FACScan; Becton Dickinson, San Jose, Calif., USA).

Polyarginine and polylysine proved to be the most effective adjuvants; polyornithine exhibited a cytotoxic effect under the conditions chosen. The increase in peptide uptake caused by the polyarginine and polylysine correlates with the concentration (FIG. 15 d, e); the uptake increases with the chain length (FIG. 16).

Figure 15C:
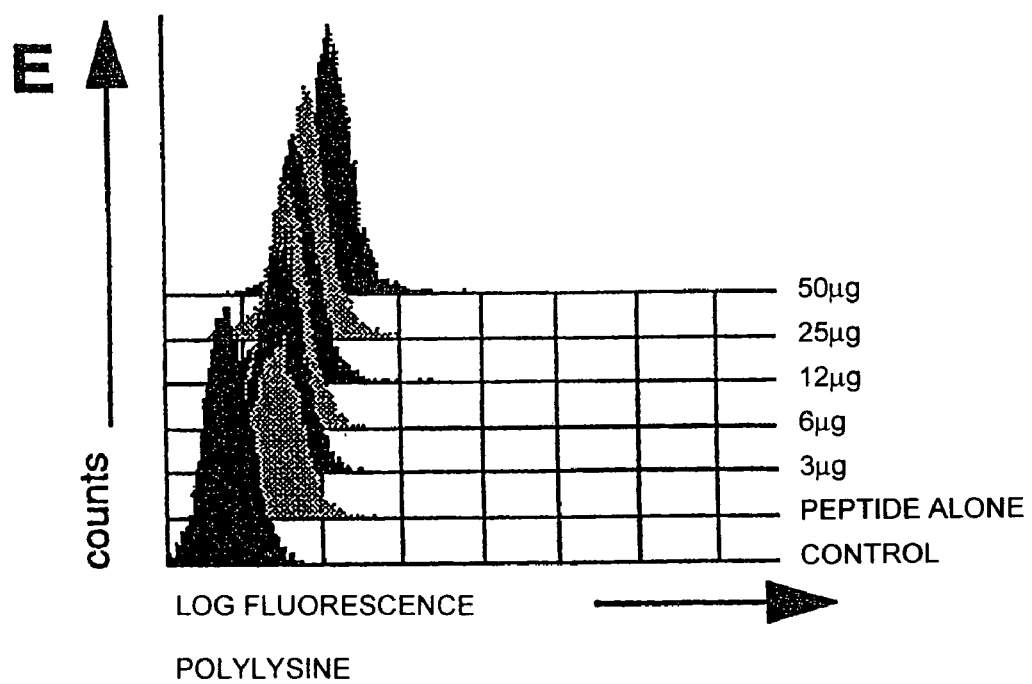
FIG. 15: Increase in transportation of peptides into antigen-presenting cells by means of polycationic polyamino acids and histones
Figure 17:
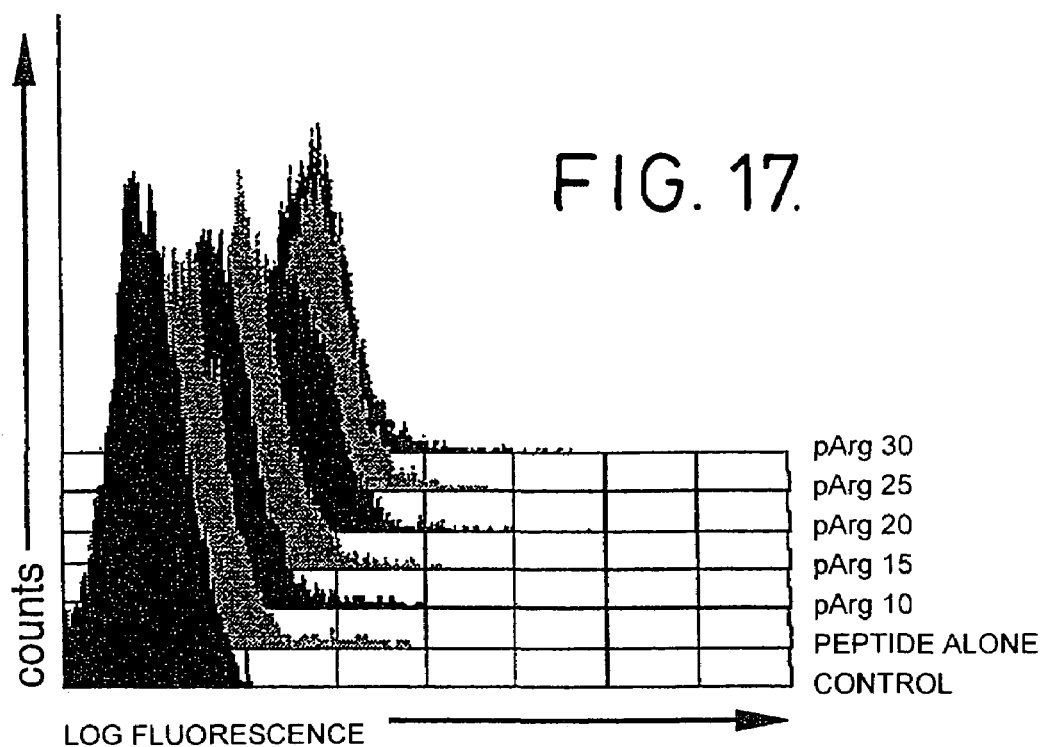
FIG. 17: Transporting of peptides with polyarginines of low molecular weight

It was observed that polyarginine, with an increase of 3 powers of ten compared with the control, has a wider suitable concentration range than polylysine, which showed a maximum increase of less than 2 powers of ten, and that with all the chain lengths used it is more effective for transporting proteins than polylysine (FIG. 16): Polyarginine allows efficient transport at concentrations as low as 3 µg/ml, whereas for polylysine concentrations of >25 µg/ml were needed in order to obtain a significant increase in fluorescence (FIG. 15 d, e).

b) In order to establish whether there is a lower limit of chain length for the peptide transportation, polyarginines of different chain lengths (10–30 groups) were synthesised and tested for their ability to increase the peptide transport at high concentrations of the polycations (FIG. 17). For these experiments the peptide LFEAIEGFI (SEQ ID NO:1) was used the polyarginine polymers tested were used in a concentration of 100 µg/ml.

An increase, albeit a slight one, in the peptide transportation was observed even with the shortest polyarginine tested.

c) Basic amino acids are positively charged molecules. It can therefore be assumed that negatively charged peptides could bind to these polycations via electrostatic interactions, which might possibly lead to an increased peptide uptake. To test this hypothesis, the ability of cationic polyamino acids to absorb short peptides into P388D1 cells as a function of their charge was compared. The Table which follows lists the negatively charged peptides used which satisfy all the conditions required for MHC-I binding (Ranmensee et al., 1995). Peptide 1 is derived from murine TRP (tyrosine related protein), peptide 2 is derived from influenza haemagglutinin (Schmidt et al., 1996), peptide 3 from murine tyrosinase, peptide 4 from P198 tumour antigen, peptide 5 from beta-galactosidase (Gavin et al., 1993). ("Mr"denotes molecular weight range, "fluor" denotes fluorescein).

TABLE

| sequence | Mr | Mr fluor | charge | charge + fluor |
|---|---|---|---|---|
| YAEDYEEL | 1031 | 1389 | 4 × negative | 6 × negative |
| LFEAIEGFI | 1038 | 1396 | 2 × negative | 4 × negative |
| IFMNGTMSQV | 1127 | 1485 | neutral | 2 × negative |
| KYQAVTTTL | 1024 | 1382 | 1 × positive | 1 × negative |
| TPHPARIGL | 961 | 1319 | 2 × positive | neutral |

Figure 18:
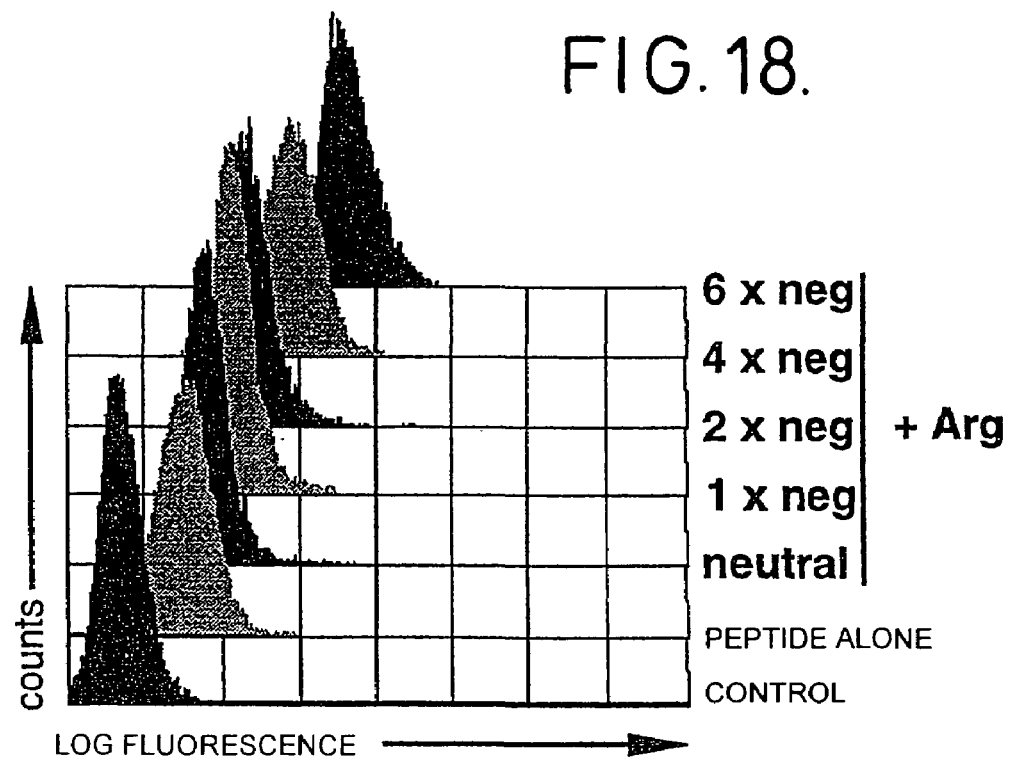
FIG. 18: Influence on transport efficiency as a function of the charging of the peptide In the Examples which follow, the following materials and methods were used unless otherwise stated.

Because of the method used to label the peptide with fluorescein, two negative charges were introduced. It was found that after incubation with polyarginine the peptides (5 nmol per sample) with the highest number of negative charges were transported most efficiently into P388D1 cells, which indicates that an ionic interaction between peptide and polycation further increases the transportation of peptide into cells (FIG. 18). However, compared with cells which were treated with peptide alone, larger quantities were absorbed in the case of neutral peptides in the presence of the polycations. Treatment with peptide alone resulted in virtually identical fluorescence signals with all the peptides tested; for reasons of representation, the fluorescence signal obtained with peptide LFEAIEGFI (SEQ ID NO:1) is shown in FIG. 18 as "peptide alone" in a representative capacity.

BIBLIOGRAPHY

Alexander, J. et al., 1989, Immunogenetics 29, 380
Allred, D. C. et al., 1992, J. Clin. Oncol. 10 (4), 599–605
Avrameas, A. et al., 1996, Eur. J. Immunol. 26, 394–400
Behr, J. P., 1994, Bioconjug-Chem., September–October, 5(5), 382–9
Bertoletti, A. et al., 1994, Nature 369, 407–410
Biologic Therapy of Cancer, Editors: DeVita, V. T. Jr., Hellman, S., Rosenberg, S. A., Verlag J. B. Lippincott Company, Philadelphia, New York, London, Hagerstown
Blomberg, K. and Ulfstedt, A. C., 1993, J. Immunol. Methods 160:27–34
Boon, T., 1992, Adv Cancer Res 58, 177–210
Boon, T., 1993, Spektrum der Wissenschaft (May), 58–66
Boon, T. et al., 1994, Annu. Rev. Immunol. 12, 337–65
Boon, T. and van der Bruggen, P., 1996, J Exp Med 183, 725–729
Braciale, T. J. and Braciale, V. L., 1991, Immunol. Today 12, 124–129
Brocke, S. et al., 1996, Nature 379 (6563), 343–346
Bronte, et al., 1995, J. Immunol. 154, 5282
Carrel, S. and Johnson, J. P., 1993, Current Opinion in Oncology 5, 383–389
Coligan, J. E., et al., 1991, Nature 351, 290–296
Coligan, J. E., et al., 1991, Current Prot. in Immunol., Wiley, New York
Coulie, P. G. et al., 1992, Int. J. Cancer, 50, 289–297
Coulie, P. G. et al., 1995, Proc Natl Acad Sci USA 92, 7976–80

Coulie, P. G. et al., 1994, J. Exp. Med. 180, 35–42
Cox, A. L. et al., 1994, Science 264, 5159, 716–9
Current Protocols im Molecular Biology, 1995, Editor: Ausubel F. M., et al., John Wiley & Sons, Inc.
Dranoff, G. et al., 1993, Proc. Natl. Acad. Sci. USA 90, 3539–3543
Dranoff, G. and Mulligan, R. C., 1995, Advances in Immunology 58, 417
Falk, K. et al., 0.1991, Nature 351, 290–296
Feigner, J. H. et al., 1994, J. Biol. Chem. 269, 2550–2561
Feltkamp, M. C. et al., 1995, Eur. J. Immunol. 25 (9), 2638–2642
Fenton, R. G. et al., 1993, J. Natl. Cancer Inst. 85, 16, 1294–302
Fisk, B. et al., 1995, J. Exp. Med. 1881, 2109–2117
Flow Cytometry, Acad. Press, Methods in Cell Biology, 1989, Vol. 0.33, Editor: Darzynkiewicz, Z. and Crissman, H. A.
Gedde Dahl, T. et al., 1992, Hum Immunol. 33, 4, 266–74
Grohmann, U. et al., 1995, Eur. J. Immunol. 25, 2797–2802
Guarini, A. et al., 1995, Cytokines and Molecular Therapy 1, 57–64
Han, X. K. et al., 1995, PNAS 92, 9747–9751
Handbook: FACS Vantage™ User's Guide, April 1994, Becton Dickinson
Handbook: CELL Quest™ Software User's Guide, June 1994, Becton Dickinson
Henderson, R. A., and Finn, O. J. 1996, Advances in Immunology 62, 217–256
Hérin M. et al., 1987, Int. J. Cancer, 39, 390
Hock, H. et al., 1993, Cancer Research 53, 714–716
Houbiers, J. G., et al., 1993; Eur J Immunol 23, 2072–7.
Huang, A. Y. C., and Pardoll, D. M. (1996). Proc Natl Acad Sci USA 93, 9730–5
Inaba, K., et al., 1992, J Exp Med 176, 1693–1702
Jung, S. et al., 1991, J. Exp. Med. 173, 1, 273–6
Kawakami, Y. et al., 1994, Proc. Natl. Acad. Sci. USA 91, 6458–62
Kawakami, Y. et al., 1994a, Proc. Natl. Acad. Sci. USA 91, 9, 3515–9
Kawakami, Y. et al., 1994b, J. Exp. Med. 180, 1, 347–52
Kawakami, Y. et al., 1995, The Journal of Immunol. 154, 3961–3968
Kärre, K. et al., 1986, Nature 319, 20. February, 675
Kersh, G. J. et al., 1996, Nature 380 (6574), 495–498
Kovacsovics Bankowski, M. and Rock, K. L., 1995, Science 267, 243–246
Lanzavecchia, A., 1996, Curr. Opin. Immunol. 8, 348–354
Lehmann, J. M. et al., 1989, Proc. Natl. Acad. Sci. USA 86, 9891–9895
Lethe, B. et al., 1992, Eur. J. Immunol. 22, 2283–2288
Li, H., et al., 1989, J Exp Med 169, 973–986
Lill, N. L., Tevethia, M. J., Hendrickson, W. G., and Tevethia, S. S. (1992). J Exp Med 176, 449–57
Ljunggren, H. G., et al., 1990, Nature 346:476–480
Loeffler, J. -P. et al., 1993, Methods Enzymol. 217, 599–618
Lopez, J. A., et al., 1993, Eur. J. Immunol. 23, 217–223
MacBroom, C. R. et al., 197.2, Meth. Enzymol. 28, 212–219
Mackiewicz, A. et al., 1995, Human Gene Therapy 6, 805–811
Malnati, M. S. et al., 1995, Science 267, 1016–1018
Mandelboim, O. et al., 1994, Nature 369, 5.May, 67–71
Mandelboim, O. et al., 1995, Nature Medicine 1, 11, 1179–1183
Marchand, M., et al., 1995, Int J of Cancer 63, 883–5
McIntyre, C. A., 1996 Cancer Immunol.Immunother. 42:246–250.
Midoux, P., et al., 1993, NATO ASI Series H67, 49–64
Morishita, R. et al., 1993, J. Clin. Invest. 91, 6, 2580–5
Nabel, G. J. et al., 1993, Proc. Natl. Acad. Sci. USA 90, 11307–11311
Noguchi, Y. et al., 1994. Proc Natl Acad Sci USA 91, 3171–3175
Oettgen, H. F. and Old, L. J., 1991, Biologic Therapy of Cancer, Editors: DeVita, V. T. Jr., Hellman, S., Rosenberg, S. A., Verlag J. B. Lippincott Company, Philadelphia, New York, London, Hagerstown, 87–119
Ostrand-Rosenberg, S., 1994, Current Opinion in Immunology 6, 722–727
Pardoll, D. M., 1993, Immunology Today 14, 6, 310
Practical Immunology, Editors: Leslie Hudson and Frank C. Hay, Blackwell Scientific Publications, Oxford, London, Edinburgh, Boston, Melbourne
Peace, D. J. et al., 1991, J. Immunol. 146, 6, 2059–65
Peoples, G. E. et al., 1994, J. Immunol. 152, 10, 4993–9
Plautz, G. E. et al., 1993, Proc. Natl. Acad. Sci. USA 90, 4645–4649
Porgador, A., Gilboa, E., 1995, J. Exp. Med. 182, 255–260
Puccetti, P. et al., 1995, Eur. J. Immunol. 24, 1446–1452
Rammensee, H. G., et al., 1993, Annu Rev Immunol 11, 213–44
Rammensee, H. G. et al., 1993, Current Opinion in Immunology 5, 35–44
Rammensee, H. G., et al., 1995, Current Biology 7, 85–96
Rammensee, H. G., 1995, Current Opinion in Immunology 7, 85–96
Rammensee, H. G., et al., 1995, Immunogenetics 41, 178–228
Remington's Pharmaceutical Sciences, 18. edition 1990, Mack Publishing Company, Easton, Pa. 1990
Remy, J. S. et al., 1994, Bioconjug-Chem., November–December, 5(6), 647–54
Rennie, J. and Rusting, R., 1996, Scientific American September, 28–30
Rivoltini, L. et al., 1995, The Journal of Immunology 154, 5 2257–2265
Robbins, P. F., et al., 1994, Cancer Res 54, 3124–6
Robbins, P. F., et al., 1995, J Immunol 154, 5944–50
Robbins, P. F. and Rosenberg, S. A., 1996, Journ. Exp. Med. 183, 1185–92.
Robbins, P. F. and Kawakami, Y., 1996, Curr Opin Immunol 8, 628–636
Roitt I. M., Brostoff J., Male D. K. Immunology, Churchill Livings tone
Rosenberg, S. A., 1996, Annual Reviews of Medicine, 47, 481–491
Ryser, H. J. and Hancock, R., 1965, Science 150, 501–503
Ryser, H. J. and Shen, W. C., 1978, Proc Natl Acad Sci USA 75, 3867–3870
Schmidt, W., et al., May 1995, Proc. Natl. Acad. Sci. USA, 92, 4711–4714
Schmidt, W., et al., 1996, Proc Natl Acad Sci USA, 93, 9759–63
Sette, A. et al., 1994, Mol. Immunol. 31(11):813–822,
Shen, W. C. and Ryser, H. J., 1978, Proc. Natl. Acad. Sci. USA, 75, 1872–1876
Shen, W. C. and Ryser, H. J., 1979, Mol. Pharmacol. 16, 614–622
Shen, W. C. and Ryser, H. J., 1981, Proc. Natl. Acad. Sci. USA, 78, 7589–7593
Skipper, J., and Stauss, H. J., 1993, J. Exp. Med. 177, 5, 1493–8
Slingluff, C. L. et al., 1994, Current Opinion in Immunology 6, 733–740

Stein, D. et al., 1994, EMBO Journal, 13, 6, 1331–40
Stuber, G. et al., 1994, Eur. J. Immunol 24, 765–768
Sykulev, Y. et al., 1994, Immunity 1, 15–22
Theobald, M., Levine, A. J., and Sherman, L. A. (1995) PNAS 92, 11993–7
Tibbets, L. M. et al., 1993, Cancer, Jan. 15., Vol. 71, 2, 315–321
Tykocinski, M. L. et al., 1996, Am. J. Pathol. 148, 1–16
van der Bruggen, P. et al., 1994, Eur. J. Immunol. 24, 9, 2134–40 Issn: 0014-2980
Van der Eynde, B. and Brichard, V. G., 1995, Current Opinion Immunol. 7, 674–81
Van Pel, A. and Boon, T., 1982, Proc. Natl. Acad. Sci. USA 79, 4718–4722
Van Pel, A., et al., 1995, Immunological Reviews 145, 229–250
Vitiello, A. et al, 1995, J. Clin. Inv. 95, 1, 341–349
Wagner, E., et al., 1990, Proc Natl Acad Sci USA 87, 3410–4
Wagner, E., et al., 1992, Proc Natl Acad Sci USA 89, 6099–103
Wang, R. F., et al., 1995, J Exp Med 181, 799–804
Weynants, P. et al., 1994, Int. J. Cancer 56, 826–829
Widmann, C. et al., 1992, J. Immunol. Methods 155 (1), 95–99
Wölfel, T. et al., 1994 a), Int. J. Cancer 57, 413–418
Wölfel, T. et al., 1994 b), Eur. J. Immunol. 24, 759–764
York, I. A. and Rock, K. L., 1996, Ann. Rev. Immunol. 14, 369–396
Yoshino, I. et al., 1994 a), J. Immunol. 152, 5, 2393–400
Yoshino, I. et al., 1994 b), Cancer Res., 54, 13, 3387–90
Young, J. W., Inaba, K., 1996, J. Exp. Med., 183, 7–11
Zatloukal, K. et al., 1993, Gene 135, 199–20
Zatloukal, K. et al., 1995, J. Immun. 154, 3406–3419

What is claimed is:

1. A pharmaceutical composition for treating an individual formed by mixing:
   (a) one or more antigenic peptides which fit into and bind the binding fork of an MHC molecule which is expressed by said individual; and
   (b) an adjuvant selected from a group consisting of:
      (i) polyarginine with a degree of polymerization from about 15 to about 500,
      (ii) polylysine,
      (iii) polyornithine,
      (iv) histones,
      (v) protamines,
      (vi) polyethyleneimines, and
      (vii) a mixture thereof;
   wherein said adjuvant is capable of increasing the binding of said peptides to cells of said individual and/or the entry of said peptides into the antigen-presenting cells of said individual, and wherein said adjuvant thereby brings about an increase in the immunomodulatory activity of said peptides.

2. The pharmaceutical composition of claim 1, wherein said MHC molecule is an MHC-I molecule.

3. The pharmaceutical composition of claim 1, wherein said MHC molecule is an MHC-II molecule.

4. The pharmaceutical composition of claim 1, wherein said peptides are derived from a protein of a pathogenic agent.

5. The pharmaceutical composition of claim 4, wherein said pathogenic agent is a bacterium.

6. The pharmaceutical composition of claim 4, wherein said pathogenic agent is a virus.

7. The pharmaceutical composition of claim 1, wherein said peptides are derived from a tumor antigen.

8. The pharmaceutical composition of claim 7, wherein said tumor antigen is expressed by said individual to be treated.

9. The pharmaceutical composition of claim 7, wherein said tumor antigen is a melanoma antigen.

10. The pharmaceutical composition of claim 7, which further comprises a cytokine.

11. The pharmaceutical composition of claim 10, wherein said cytokine is selected from the group consisting of: IL-2, IL-4, IL-12, IFN-α, IFN-β, IFN-γ, IFN-ω, TNF-α, and GM-CSF.

12. The pharmaceutical composition of claim 1, which comprises more than one peptide, each of which binds to different MHC-subtypes of said individual to be treated.

13. The pharmaceutical composition of claim 1, wherein said composition comprises one or more peptides which are derived from a naturally occurring immunogenic protein or tumor antigen, or a cellular breakdown product thereof.

14. The pharmaceutical composition of claim 1, wherein said composition comprises one or more peptides which are different from peptides derived from naturally occurring immunogenic proteins or tumor antigens or cellular breakdown products thereof.

15. The pharmaceutical composition of claim 1, wherein said peptide is an antagonist of a peptide which is derived from a protein which causes an autoimmune disease.

16. The pharmaceutical composition of claim 1, wherein said peptide is negatively charged.

17. The pharmaceutical composition of claim 1, wherein said adjuvant is polyarginine with a degree of polymerization from about 15 to about 500.

18. The pharmaceutical composition of claim 1, wherein said adjuvant is polylysine.

19. The pharmaceutical composition of claim 1, wherein said adjuvant is conjugated with a cellular ligand.

20. The pharmaceutical composition of claim 19, wherein said ligand is a carbohydrate group.

21. The pharmaceutical composition of claim 20, wherein said ligand is fucose.

22. The pharmaceutical composition of claim 19, wherein said ligand is transferrin.

23. The pharmaceutical composition of claim 1, wherein said composition further comprises DNA which is free from sequences which code for functional proteins.

24. The pharmaceutical composition of claim 1, wherein said composition further comprises DNA which codes for a cytokine.

25. The pharmaceutical composition of claim 24, wherein said cytokine is selected from the group consisting of IL-2, IL-4, IL-12, IFN-α, IFN-β, IFN-γ, IFN-ω, TNF-α and GM-CSF.

26. The pharmaceutical composition of claim 1, wherein said composition is mixed with a pharmaceutically acceptable carrier for parenteral administration.

27. The pharmaceutical composition of claim 1, wherein said composition is in the form of a hydrogel for topical administration.

28. The pharmaceutical composition of claim 1, wherein said adjuvant is polyornithine.

29. The pharmaceutical composition of claim 1, wherein said adjuvant is histones.

30. The pharmaceutical composition of claim 1, wherein said adjuvant is protamines.

31. The pharmaceutical composition of claim 1, wherein said adjuvant is polyethyleneimines.

32. A method for increasing the immunomodulatory activity of one or more peptides which have an immunomodulatory activity in an individual, comprising administering to said individual the composition of claim 1.

* * * * *

UNITED STATES PATENT AND TRADEMARK OFFICE
CERTIFICATE OF CORRECTION

PATENT NO.       : 7,105,162 B1                         Page 1 of 1
APPLICATION NO.  : 09/125672
DATED            : September 12, 2006
INVENTOR(S)      : Schmidt et al.

It is certified that error appears in the above-identified patent and that said Letters Patent is hereby corrected as shown below:

On the Title page, column 1, section [86], please delete "Apr. 26, 1999" and insert therein -- Sep. 15, 1998 --.

Signed and Sealed this

Third Day of April, 2007

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Leu Phe Glu Ala Ile Glu Gly Phe Ile
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Phe Phe Ile Gly Ala Leu Glu Glu Ile
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Lys Tyr Gln Ala Val Thr Thr Thr Leu
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4
```

```
Ser Tyr Phe Pro Glu Ile Thr His Ile
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ala Ser Asn Glu Asn Met Glu Thr Met
 1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Pro Pro His Ser Asn Asn Phe Gly Tyr
 1               5                  10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Ile Ser Thr Gln Asn His Arg Ala Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Leu Pro Tyr Leu Gly Trp Leu Val Phe
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Arg Tyr Ala Glu Asp Tyr Glu Glu Leu
 1               5

<210> SEQ ID NO 10
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      Peptide

<400> SEQUENCE: 10

Pro Tyr Leu Glu Gln Ala Ser Arg Ile
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Tyr Tyr Val Ser Arg Asp Thr Leu Leu
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Tyr Tyr Ser Val Lys Lys Thr Phe Leu
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Tyr Ala Glu Asp Tyr Glu Glu Leu
 1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Ile Phe Met Asn Gly Thr Met Ser Gln Val
 1               5                  10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Thr Pro His Pro Ala Arg Ile Gly Leu
 1               5
```